US011235066B2

(12) United States Patent
Wang et al.

(10) Patent No.: US 11,235,066 B2
(45) Date of Patent: Feb. 1, 2022

(54) MICELLES AND METHODS

(71) Applicant: THE REGENTS OF THE UNIVERSITY OF MICHIGAN, Ann Arbor, MI (US)

(72) Inventors: Thomas D. Wang, Ann Arbor, MI (US); Supang Khondee, Phayao (TH)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 414 days.

(21) Appl. No.: 15/780,277

(22) PCT Filed: Dec. 1, 2016

(86) PCT No.: PCT/US2016/064472
§ 371 (c)(1),
(2) Date: May 31, 2018

(87) PCT Pub. No.: WO2017/096076
PCT Pub. Date: Jun. 8, 2017

(65) Prior Publication Data
US 2018/0360988 A1 Dec. 20, 2018

Related U.S. Application Data

(60) Provisional application No. 62/262,195, filed on Dec. 2, 2015.

(51) Int. Cl.
| *A61K 47/69* | (2017.01) |
| *C08G 69/40* | (2006.01) |
| *C08G 69/10* | (2006.01) |
| *C08G 81/00* | (2006.01) |
| *A61K 9/107* | (2006.01) |
| *A61K 47/62* | (2017.01) |
| *A61K 47/60* | (2017.01) |
| *A61K 47/54* | (2017.01) |
| *A61P 35/00* | (2006.01) |
| *A61K 31/436* | (2006.01) |
| *C08G 65/334* | (2006.01) |

(52) U.S. Cl.
CPC ........ *A61K 47/6907* (2017.08); *A61K 9/1075* (2013.01); *A61K 31/436* (2013.01); *A61K 47/554* (2017.08); *A61K 47/60* (2017.08); *A61K 47/62* (2017.08); *A61P 35/00* (2018.01); *C08G 65/3348* (2013.01); *C08G 69/10* (2013.01); *C08G 69/40* (2013.01); *C08G 81/00* (2013.01)

(58) Field of Classification Search
None
See application file for complete search history.

(56) References Cited

U.S. PATENT DOCUMENTS

2012/0219505 A1    8/2012  Wang et al.

FOREIGN PATENT DOCUMENTS

| WO | WO 2008/073856 | * | 6/2008 |
| WO | WO-2010/054266 A2 | | 5/2010 |
| WO | WO 2012/087913 | * | 6/2012 |
| WO | WO 2013/096388 | * | 6/2013 |
| WO | WO-2016/029125 A1 | | 2/2016 |

OTHER PUBLICATIONS

Xiao et al. ('OA02 peptide facilitates the precise targeting of paclitaxel-loaded micellar nanoparticles to ovarian cancer in vivo' Cancer Research v72(8) Apr. 15, 2012 pp. 2100-2110) (Year: 2012).*
Hu et al., "Preparation and characterization of self-assembled nanoparticles of the novel carboxymethyl pachyman-deoxycholic acid conjugates," Carbohydrate Polymers 74:220-227 (2008).
Jiang et al., "Polymer Micellar Aggregates of Novel Amphiphilic Biodegradable Graft Copolymer Composed of Poly(aspartic acid) Derivatives: Preparation, Characterization, and Effect of pH on Aggregation," Journal of Applied Polymer Science 99:2702-2709 (2006).
Lee et al., "Poly(amino acid)s micelle-mediated assembly of magnetite nanoparticles for ultra-sensitive long-term MR imaging of tumors," Chem. Commun. 46:3559-3561 (2010).
Liu et al., "Synthesis of amphiphilic polyaspartamide derivatives and construction of reverse micelles," RSC Adv. 4:37310-37137 (2014).
Ngawhirunpat et al., "Incorporatio methods for cholic acid chitosan-g-mPEG self-assembly micellar system containing camptothecin," Colloids and Surfaces B: Biointerfaces 74:253-259 (2009).
Park et al., "Preparation and Characterization of Self-Assembled Nanoparticles of Heparin-Deoxycholic Acid Conjugates," Langmuir 20:11726-11731 (2004).

(Continued)

Primary Examiner — Ronald T Niebauer

(74) Attorney, Agent, or Firm — Marshall, Gerstein & Borun LLP

(57) ABSTRACT

The present invention relates to micelle drug carriers and methods of using the micelles to deliver drugs to target cells. The micelles are useful, for example, for carrying and targeting drugs for the treatment of cancer to cancer cells. As one example, the disclosure provides pegylated octadecyl lithocholate micelles that are labeled with a peptide ligand for colorectal neo-plasia and that carry the small molecule mTOR inhibitor rapamycin to colorectal cancer cells.

11 Claims, 10 Drawing Sheets
Specification includes a Sequence Listing.

(56) References Cited

OTHER PUBLICATIONS

Shen et al., "Synthesis and characterization of low molecular weight hyaluronic acid-based cationic micelles for efficient siRNA delivery," Carbohydrate Polymers 77:95-104 (2009).
Choudhury et al., "Drug-Associated Renal Dysfunction and Injury," Nat. Clin. Pract. Nephrol. 2:80-91 (2006).
Fang et al., "Phosphatidic acidmediated mitogenic activation of mTOR signaling," Science 294:1942-1945 (2001).
Fields et al., "Solid phase peptide synthesis utilizing 9-?uorenylmethoxycarbonyl amino acids," Int. J. Pept. Protein Res. 35:161-214 (1990).
Fujishita et al., "Inhibition of the mTORC1 pathway suppresses intestinal polyp formation and reduces mortality in Apc716 mice," Proc. Natl. Acad. Sci. 105:13544-13549 (2008).
Garg et al., "pH-Sensitive PEGylated liposomes functionalized with a ?bronectin-mimetic peptide show enhanced intracellular delivery to colon cancer cells," Curr. Pharm. Biotechnol. 12:1135-1143 (2011).
Guo et al., "Core/shell pH-sensitive micelles self-assembled from cholesterol conjugated oligopeptides for anticancer drug delivery," AIChE J. 56:1922-1931 (2010).
Hasenstein et al., "Antitumor activity of Triolimus: a novel multidrug-loaded micelle containing paclitaxel, rapamycin, and 17-AAG," Mol. Cancer Ther. 11:2233-2242 (2012).
Hensley et al., "Endoscopic imaging and size estimation of colorectal adenomas in the multiple intestinal neoplasia mouse," Gastrointest. Endosc. 69:742-749 (2009).
International Search Report and Written Opinion from International Application No. PCT/US2016/64472 dated Apr. 28, 2017.
Interntional Preliminary Reporton Patentability from International Application No. PCT/US2016/064472 dated Jun. 5, 2018.
John et al., "Renal toxicity of therapeutic drugs," J. Clin. Pathol. 62:505-515 (2009).
Khondee et al., "Targeted therapy of colorectal neoplasia with rapamycin in peptide-labeled pegylated octadecyl lithocholate micelles," J Control Release 1999:114-121 (2015).

Kim et al., "Physicochemical characterizations of self-assembled nanoparticles of glycol chitosan-deoxycholic acid conjugates," Biomacromolecules 6:1154-1158 (2005).
Koehl et al., "Rapamycin inhibits oncogenic intestinal ion channels and neoplasia in APC$^{Min/+}$ mice," Oncogene 29:1553-1560 (2010).
Kwon et al., "Physicochemical characteristics of self-assembled nanoparticles based on glycol chitosan bearing 5ßcholanic acid," Langmuir 19:10188-10193 (2003).
Loh et al., "Drug-Induced Kidney Disease-Pathology and Current Concepts," Ann. Acad. Med. Singap. 38:240-250 (2009).
Mamot et al., "EGFR-targeted immunoliposomes derived from the monoclonal antibody EMD72000 mediate specific and effcient drug delivery to a variety of colorectal cancer cells," J. Drug Target. 14:215-223 (2006).
Miller et al., Multimodal imaging of growth and rapamycin-induced regression of colonic adenomas in ape mutation-dependent mouse, Translational oncology 5:313-320 (2012).
Shah et al., "A rapamycin-binding protein polymer nanoparticle shows potent therapeutic activity in suppressing Autoimmune dacryoadenitis in a mouse model of Sjogren's syndrome," J. Control. Release 171:269-279 (2013).
Tol et al., "Monoclonal antibodies in the treatment of metastatic colorectal cancer: a review," Clin. Ther. 32 437-453 (2010).
Wang et al., "Targeting nanoparticles to cancer," Pharmacol. Res. 62:90-99 (2010).
Weickhardt et al., "Dual Targeting of the Epidermal Growth Factor Receptor Using the Combination of Cetuximab and Erlotinib: Preclinical Evaluation and Results of the Phase II DUX Study in Chemotherapy-Refractory, Advanced Colorectal Cancer," J. Clin. Oncol. 30:1505-1512 (2012).
Yao et al., "Proliferation of colorectal cancer is promoted by two signaling transduction expression patterns: ErbB2/ErbB3/AKT and MET/ErbB3/MAPK," PLoS One 8(10):e78086 (2013).
Zhang et al., "Polymeric Micelles: Nanocarriers for Cancer-Targeted Drug Delivery," AAPS PharmSciTech 15(4):862-871 (2014).
Zhou et al., "Synthesis and characterization of amphiphilic glycidol-chitosan-deoxycholic acid nanoparticles as a drug carrier for doxorubicin," Biomacromolecules 11:3480-3486 (2010).

* cited by examiner

SEQUENCE LISTING

```
<160> NUMBER OF SEQ ID NOS: 73

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide

<400> SEQUENCE: 1

Asn Gly Thr Thr Ser Ser Asn Asn Gln Leu Ile Asn Glu Asn Asn Ile
1               5                   10                  15

Gln Asn

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide

<400> SEQUENCE: 2

Glu His Met Tyr Asn Thr Pro His Thr Tyr His Thr Thr Met Lys Asn
1               5                   10                  15

Asn Lys

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Gln Pro Ile His Pro Asn Asn Met
1               5

<210> SEQ ID NO 4
<211> LENGTH: 8
<212> TYPE: PRT
<213> ORGANISM: Artificial Sequence
```

-continued

```
<220> FEATURE:
<223> OTHER INFORMATION: Synthetic peptide

<400> SEQUENCE: 4

Asn Lys Leu Ala Ala Ala Leu Glu
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Lys Asn Tyr Lys Asn
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Thr Asn Thr His Asn
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Lys His Thr Asn Asn
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide

<400> SEQUENCE: 8

Ser Ile Leu Pro Tyr Pro Tyr
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Lys Cys Cys Phe Pro Ala Gln
1               5

<210> SEQ ID NO 10
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 10

Tyr Arg Ala Pro Trp Pro Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic peptide

<400> SEQUENCE: 11

Gln Pro Trp Pro Thr Ser Ile
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Trp Pro Thr Pro Pro Tyr Ala
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Met His Ala Pro Pro Phe Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Val Arg Pro Thr Leu Pro Met
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

Asn Phe Met Glu Ser Leu Pro Arg Leu Gly Met His
1               5                   10

<210> SEQ ID NO 16
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 16

His Tyr Lys Leu
1

<210> SEQ ID NO 17
<211> LENGTH: 7
<212> TYPE: PRT
<213> ORGANISM: Artificial Sequence
<220> FEATURE:
<223> OTHER INFORMATION: Synthetic peptide

<400> SEQUENCE: 17

Ala Lys Pro Gly Tyr Leu Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

Leu Thr Thr His Tyr Lys Leu
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic peptide

<400> SEQUENCE: 19

Gln Arg His Lys Pro Arg Glu
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic peptide

<400> SEQUENCE: 20

His Ala His Arg Ser Trp Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic peptide

<400> SEQUENCE: 21

Tyr Leu Thr Met Pro Thr Pro
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 22

Thr Tyr Pro Ile Ser Phe Met
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic peptide

<400> SEQUENCE: 23

Lys Leu Pro Gly Trp Ser Gly
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide

<400> SEQUENCE: 24

Ile Gln Ser Pro His Phe Phe
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic peptide

<400> SEQUENCE: 25

Tyr Ser Ile Pro Lys Ser Ser
1               5

<210> SEQ ID NO 26
<211> LENGTH: 12
<212> TYPE: PRT
<213> ORGANISM: Artificial Sequence
<220> FEATURE:
<223> OTHER INFORMATION: Synthetic peptide

<400> SEQUENCE: 26

Ser His Arg Asn Arg Pro Arg Asn Thr Gln Pro Ser
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide

<400> SEQUENCE: 27

Asn Arg His Lys Pro Arg Glu Lys Thr Phe Thr Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide

<400> SEQUENCE: 28
```

Thr Ala Val Pro Leu Lys Arg Ser Ser Val Thr Ile
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic peptide

<400> SEQUENCE: 29

Gly His Thr Ala Asn Arg Gln Pro Trp Pro Asn Asp
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic peptide

<400> SEQUENCE: 30

Leu Ser Leu Thr Arg Thr Arg His Arg Asn Thr Arg
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Synthetic peptide

<400> SEQUENCE: 31

Arg His Arg Asp Thr Gln Asn His Arg Pro Thr Asn
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic peptide

<400> SEQUENCE: 32

Ala Arg His Arg Pro Lys Leu Pro Tyr Thr His Thr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Synthetic peptide

<400> SEQUENCE: 33

Lys Arg Pro Arg Thr Arg Asn Lys Asp Glu Arg Arg
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic peptide

<400> SEQUENCE: 34

```
Ser Pro Met Pro Gln Leu Ser Thr Leu Leu Thr Arg
1               5                   10
```

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

```
Asn His Val His Arg Met His Ala Thr Pro Ala Tyr
1               5                   10
```

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide

<400> SEQUENCE: 36

```
Arg Thr Ser Pro Ser Ser Arg
1               5
```

<210> SEQ ID NO 37
<211> LENGTH: 7
<212> TYPE: PRT
<213> ORGANISM: Artificial Sequence
<220> FEATURE:
<223> OTHER INFORMATION: Synthetic peptide

<400> SEQUENCE: 37

```
His Leu Gln Leu Gln Arg Leu
1               5
```

<210> SEQ ID NO 38
<211> LENGTH: 7
<212> TYPE: PRT
<213> ORGANISM: Artificial Sequence
<220> FEATURE:
<223> OTHER INFORMATION: Synthetic peptide

<400> SEQUENCE: 38

```
Ile Gln Thr Asn Pro Thr Met
1               5
```

<210> SEQ ID NO 39
<211> LENGTH: 7
<212> TYPE: PRT
<213> ORGANISM: Artificial Sequence
<220> FEATURE:
<223> OTHER INFORMATION: Synthetic peptide

<400> SEQUENCE: 39

```
Arg Ser Leu Thr Gln Gln Thr
1               5
```

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

```
Ser Leu Gln His Leu Arg Ser
```

```
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic peptide

<400> SEQUENCE: 41

Ile Gln Leu Lys Ile Asn Ser
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic peptide

<400> SEQUENCE: 42

Ile Thr Ile Arg Gln His Ile
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Arg Arg Ser Asn Ser Gln Leu
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic peptide

<400> SEQUENCE: 44

Leu Asn Arg Ile Arg Arg Arg
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic peptide

<400> SEQUENCE: 45

Asn Asn Met Lys Lys Ile Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Leu Gln Ser Leu Ile Ser Lys
1               5
```

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Ile His Thr Arg Arg Arg Lys
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Arg Pro Asn Lys Pro Arg Ile
1               5

<210> SEQ ID NO 49
<211> LENGTH: 7
<212> TYPE: PRT
<213> ORGANISM: Artificial Sequence
<220> FEATURE:
<223> OTHER INFORMATION: Synthetic peptide

<400> SEQUENCE: 49

Arg His Arg Arg Ser Pro Ile
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Ile Thr Leu Ser Ile Thr Gln
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Lys Thr Gln Leu Met Ile Ile
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Arg Pro Arg Gln Leu Gln Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Thr Arg Arg His Thr Ile Ile
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Arg Ile Ile His Lys Asn Met
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide

<400> SEQUENCE: 55

Leu Leu Thr Ile Ser Pro Lys
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Leu Leu Pro Met His Met Asn
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Thr Ser Pro Met Leu Ser Ile
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic peptide

<400> SEQUENCE: 58

Leu Arg Asn Asn Ile Arg His
1               5

-continued

```
<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Lys Ser Pro Asn Pro Arg Phe
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Arg His Pro Phe Pro Arg Phe
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

<400> SEQUENCE: 61

Arg His Pro Trp Pro Asn Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic peptide

<400> SEQUENCE: 62

Arg His Pro Tyr Pro Gln Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Arg Lys Pro Phe Pro Arg His
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Tyr Thr Thr Thr Asn Ala Ser
1               5

<210> SEQ ID NO 65
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Asp Asn Glu Pro Ile Ala Gln
1               5

<210> SEQ ID NO 66
<211> LENGTH: 13
<212> TYPE: PRT
<213> ORGANISM: Artificial Sequence
<220> FEATURE:
<223> OTHER INFORMATION: Synthetic peptide

<400> SEQUENCE: 66

Gln Pro Ile His Pro Asn Asn Met Gly Gly Gly Ser Lys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic peptide

<400> SEQUENCE: 67

Lys Cys Cys Phe Pro Ala Gln Gly Gly Gly Ser Lys
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic peptide

<400> SEQUENCE: 68

Leu Thr Thr His Tyr Lys Leu Gly Gly Gly Ser Lys
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic peptide

<400> SEQUENCE: 69

Ala Lys Pro Gly Tyr Leu Ser Gly Gly Gly Ser Lys
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic peptide

<400> SEQUENCE: 70

Tyr Thr Thr Thr Asn Ala Ser Gly Gly Gly Ser Lys
1               5                   10

<210> SEQ ID NO 71
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 71

Asp Asn Glu Pro Ile Ala Gln Gly Gly Gly Ser Lys
1               5                   10

<210> SEQ ID NO 72
<211> LENGTH: 5
<212> TYPE: PRT
<213> ORGANISM: Artificial Sequence
<220> FEATURE:
<223> OTHER INFORMATION: Synthetic peptide

<400> SEQUENCE: 72

Gly Gly Gly Ser Lys
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide

<400> SEQUENCE: 73

Tyr Thr Thr Asn Lys His
1               5
```

MICELLES AND METHODS

CROSS REFERENCE TO RELATED APPLICATIONS

This application is a U.S. National Phase of PCT/US2016/064472, filed Dec. 1, 2016, which claims the benefit of U.S. Provisional Patent Application Ser. No. 62/262,195, filed Dec. 2, 2015, which are incorporated herein by reference in their entireties.

STATEMENT OF GOVERNMENT INTEREST

This invention was made with government support under grant numbers CA136429 and CA142750 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 13,839 byte ASCII (Text) file named "49220PCT_SeqListing.txt," created on Dec. 1, 2016.

FIELD OF THE INVENTION

The present invention relates to micelle drug carriers and methods of using the micelles to deliver drugs to target cells. The micelles are useful, for example, for carrying drugs to target organs for the treatment of cancers. As one example, the disclosure provides pegylated octadecyl lithocholate micelles that are labeled with a peptide ligand for colorectal neoplasia and that carry the small molecule mTOR inhibitor rapamycin to colorectal cancer cells.

BACKGROUND

Worldwide, more than 1.36 million individuals are diagnosed with colorectal cancer (CRC) each year. These numbers are expected to nearly double over the next 20 years, as obesity is increasing in epidemic proportions and more developing countries are adopting Western diets. Surgery is the first choice for therapy in patients with early CRC. Adjuvant chemotherapy, most frequently 5-fluorouracil (5-FU), oxaliplatin, andirinotecan, is commonly administered. Unfortunately, these drugs frequently incur severe side effects, such as diarrhea and neuropathy, that may result in dose reduction and limited effectiveness. Moreover, even after the visible tumor is resected, circulating cancer cells can result in cancer recurrence ~50% of the time. Targeted therapies include monoclonal antibodies[11] and small molecules[2], and have been FDA-approved for treatment of metastatic CRC. The pharmacokinetic properties of antibodies, including extravasation, diffusion, and penetration, are limited by size and reduce drug accumulation within tumors. Antibodies can also be immunogenic. Effective drugs for treatment of early CRC have also been limited by poor water solubility.

Rapamycin is a potent mTOR inhibitor that has low and unpredictable oral bioavailability[3-5]. Parenteral use of this lipophilic drug is limited by poor water solubility (2.6 µg/mL at 25° C.)[3-5] and high systemic toxicity. Free rapamycin is highly hydrophobic and dissolves minimally in organic solvents that can be harmful to non-target organs such as the liver and kidney.

Encapsulation of drugs in micelles can reduce effective volume of distribution, maximize tumor accumulation, and minimize systemic toxicity. They can be labeled with a targeting moiety to improve specific drug delivery and cellular internalization. Deoxycholic acid and their derivatives have been used to modify chitosan for use as nanocarriers of cancer therapy[3]. Micelles are have been used for packaging hydrophobic agents. By partitioning the drug within its core, micelles can increase drug loading, extend drug release, and improve plasma half-life[3,4]. These agents form spontaneously by self-assembly and degrade within tumor cells[3-5].

There remains a need in the art for products and methods for encapsulating drugs, for example, for use in treating CRC.

SUMMARY

Provided herein are targeted micelle drug carriers. An exemplary targeted micelle drug carrier useful for treating CRC is a pegylated octadecyl lithocholate micelle labeled with a peptide ligand for colorectal neoplasia that encapsulates rapamycin.

More generally, the disclosure provides a micelle comprising block co-polymers of the structure A-B-C, wherein hydrophobic component A is a bile acid, hydrophilic component B is a polymer and C is a targeting peptide.

The bile acid component A of the micelles may be, for example, octadecyl lithocholate, cholic acid, chenodeoxycholic acid, glycocholic acid or deoxycholic acid.

The hydrophilic polymer component B of the micelles may be, for example, methoxy poly(ethylene) glycol (PEG) amine or thiol PEG amine.

The targeting peptide component C binds to a target of interest including, but not limited to, a specific type of cell. The targeting peptide component C may, for example, bind to a colorectal cell. Exemplary peptides targeting colorectal neoplasia include, but are not limited to:

```
a peptide
                                   (SEQ ID NO: 1)
NGTTSSNNQLINENNIQN, (SEQ ID NO: 2)
EHMYNTPHTYHTTMKNNK, (SEQ ID NO: 3)
QPIHPNNM, (SEQ ID NO: 4)
NKLAAALE, (SEQ ID NO: 5)
KNYKN, (SEQ ID NO: 6)
TNTHN, (SEQ ID NO: 7)
KHTNN, (SEQ ID NO: 8)
SILPYPY, (SEQ ID NO: 9)
KCCFPAQ,
```

-continued

YRAPWPP, (SEQ ID NO: 10)

QPWPTSI, (SEQ ID NO: 11)

WPTPPYA, (SEQ ID NO: 12)

MHAPPFY, (SEQ ID NO: 13)

VRPTLPM, (SEQ ID NO: 14)

NFMESLPRLGMH, (SEQ ID NO: 15)

HYKL, (SEQ ID NO: 16)

AKPGYLS (SEQ ID NO: 17)
or

LTTHYKL; (SEQ ID NO: 18)

an EGFR-specific peptide

QRHKPRE, (SEQ ID NO: 19)

HAHRSWS, (SEQ ID NO: 20)

YLTMPTP, (SEQ ID NO: 21)

TYPISFM, (SEQ ID NO: 22)

KLPGWSG, (SEQ ID NO: 23)

IQSPHFF, (SEQ ID NO: 24)

YSIPKSS, (SEQ ID NO: 25)

SHRNRPRNTQPS, (SEQ ID NO: 26)

NRHKPREKTFTD, (SEQ ID NO: 27)

TAVPLKRSSVTI, (SEQ ID NO: 28)

GHTANRQPWPND, (SEQ ID NO: 29)

LSLTRTRHRNTR, (SEQ ID NO: 30)

RHRDTQNHRPTN, (SEQ ID NO: 31)

ARHRPKLPYTHT, (SEQ ID NO: 32)

KRPRTRNKDERR, (SEQ ID NO: 33)

SPMPQLSTLLTR (SEQ ID NO: 34)
or

NHVHRMHATPAY; (SEQ ID NO: 35)

-continued a claudin-1 specific peptide

RTSPSSR, (SEQ ID NO: 36)

HLQLQRL, (SEQ ID NO: 37)

IQTNPTM, (SEQ ID NO: 38)

RSLTQQT, (SEQ ID NO: 39)

SLQHLRS, (SEQ ID NO: 40)

IQLKINS, (SEQ ID NO: 41)

ITIRQHI, (SEQ ID NO: 42)

RRSNSQL, (SEQ ID NO: 43)

LNRIRRR, (SEQ ID NO: 44)

NNMKKIT, (SEQ ID NO: 45)

LQSLISK, (SEQ ID NO: 46)

IHTRRRK, (SEQ ID NO: 47)

RPNKPRI, (SEQ ID NO: 48)

RHRRSPI, (SEQ ID NO: 49)

ITLSITQ, (SEQ ID NO: 50)

KTQLMII, (SEQ ID NO: 51)

RPRQLQR, (SEQ ID NO: 52)

TRRHTII, (SEQ ID NO: 53)

RIIHKNM, (SEQ ID NO: 54)

LLTISPK, (SEQ ID NO: 55)

LLPMHMN, (SEQ ID NO: 56)

TSPMLSI (SEQ ID NO: 57)
or

LRNNIRH; (SEQ ID NO: 58)
or a HER2-specific peptide

KSPNPRF, (SEQ ID NO: 59)

RHPFPRF, (SEQ ID NO: 60)

RHPWPNR, (SEQ ID NO: 61)

-continued

RHPYPQR (SEQ ID NO: 62)

or

RKPFPRH. (SEQ ID NO: 63)

Micelles of the disclosure carry a drug to a target cells. Exemplary drugs to be loaded in micelles include, but are not limited to, rapamycin (and other mTOR inhibitors), doxorubicin, paclitaxel, cyclosporin A, geldanamycin, dipyridamole or camptothecin.

The disclosure therefore also provides methods of treating patients in need thereof with drug-carrying micelles of the disclosure. As one example, a method of treating colorectal cancer comprising administering to the patient a micelle carrying rapamycin is contemplated.

DETAILED DESCRIPTION

Figure 1:
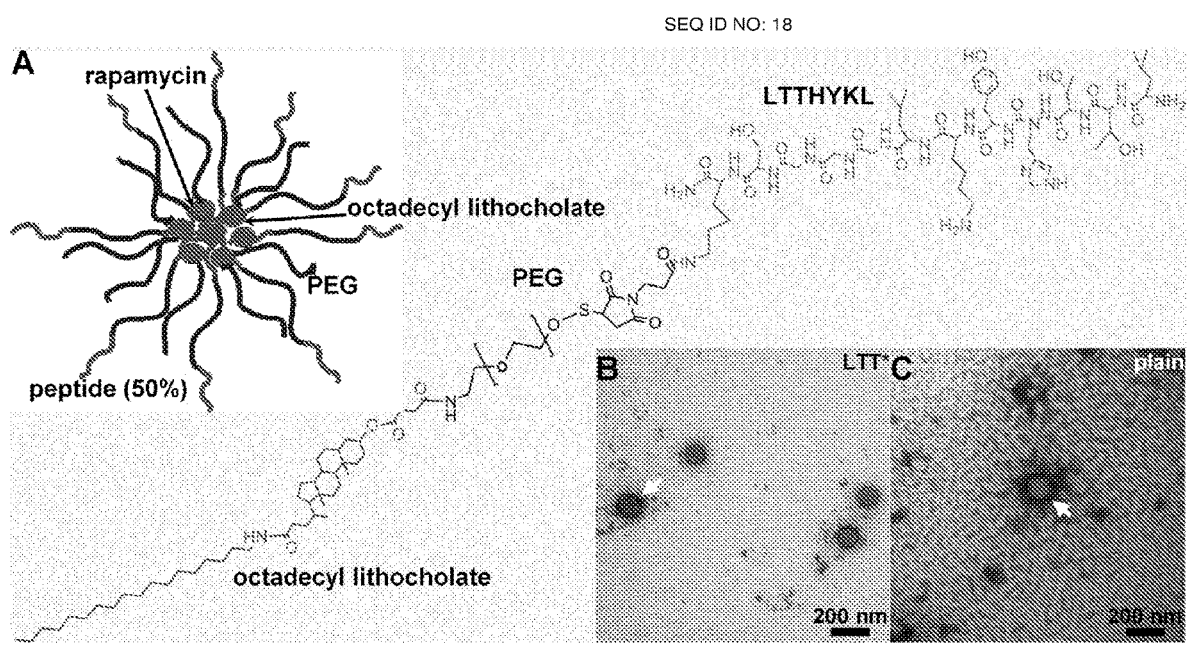
FIG. 1 shows a micelle platform for targeted drug delivery. A) Structure of rapamycin encapsulated micelle includes octadecyl lithocholate (blue), PEG (black), and LTTHYKL peptide (red) at 50% density. Transmission electron micrograph (TEM) shows morphology of B) LTT*-labeled and C) plain rapamycin micelles, scale bar 200 nm.

In one aspect, the disclosure provides a micelle carrying a hydrophobic drug in its interior and peptide components on its exterior that target the micelle to particular cell types. Block co-polymers form the micelle and have segments in the order of the formula A-B, wherein component A is hydrophobic and comprises a bile acid such as octadecyl lithocholate, while component B is hydrophilic and comprises a polymer such as heterobifunctional poly(ethylene) glycol. In some embodiments, there are a plurality of A and/or B components in the block co-polymers. In some embodiments, a linking component, X, is positioned between the A and B components. The block co-polymers self-assemble so that the hydrophobic components form the interior phase or core of the micelle and interact with the drug, while the hydrophilic polymer components form a phase or shell that interacts with the aqueous environment outside of the micelle. A targeting peptide (herein component C) is covalently linked to the hydrophilic polymer of the block co-polymer so that the order of the segments in the block co-polymer is A-B-C. Upon self-assembly of the micelles, the targeting peptides are exposed on the exterior of the micelle.

The phrase "self-assemble" refers herein to a process by which the block co-polymers are capable of arranging themselves with respect to each other in a particular way to form a micelle structure. If any additional outside intervention is required in particular cases, it will generally require only an input of energy via mechanical agitation, and potentially dissolution of a molecule in a solvent so as to aid its dispersion in an aqueous medium.

The hydrophobic component A of the block co-polymer in the micelle interacts preferentially with the hydrophobic drug. The hydrophobic component also plays a role in stabilizing the micelle structure by interacting noncovalently with the adjacent surfactant molecules. The hydrophobic component of the block co-polymer has a single chain length or a narrow distribution of chain lengths. In some embodiments, hydrophobic components include peptides having hydrophobic side chains and unnatural stepwise oligomers having hydrophobic side chains such as peptoids, oligocarbamates, oligoureas, and mixtures thereof. In some embodiments, small molecules include cholesterol, cholesterol derivatives, bile acids, bile acid derivatives, steroidal sapogenins, triterpenoid sapogenins, steroidal sapogenin derivatives, triterpenoid sapogenin derivatives, steroid derivatives, amino acids, and mixtures thereof. In some embodiments, the hydrophobic component is a bile acid. In some embodiments, the hydrophobic component is octadecyl lithocholate. In some embodiments, the hydrophobic component is cholic acid. In some embodiments, the hydrophobic component is chenodeoxycholic acid. In some embodiments, the hydrophobic component is glycocholic acid. In some embodiments, the hydrophobic component is deoxycholic acid.

The term "hydrophobic," as it refers to the hydrophobic element of block co-polymers for forming hydrophobic-core micelles that encapsulate hydrophobic drugs, means preferably having a log P value of greater than 0. Log P values measure the partitioning of a molecule between an octanol-rich and a water-rich layer in contact with one another (see CRC Handbook of Chemistry and Physics, 79.sup. edition, Lide, Ed., pp. 16-42-16-46, CRC Press, 1998; and references therein). Log P values are measured at a nominal temperature of 25° C. More preferably, hydrophobic means having a log P value greater than about 0.5, even more preferably a log P value greater than about 1, even more preferably a log P value greater than about 1.5, and most preferably a log P value greater than about 2. The term "hydrophilic," as it refers to the hydrophilic segment of block co-polymers, means having a log P value less than 0.

The hydrophilic polymer components of the micelles have a single chain length or a narrow distribution of chain lengths. In various embodiments, the polymer has a linear, branched, or cyclic structure, and/or includes side chains of gradually increasing size to generate a cone-like shape. Suitable oligomers or polymers include oligosaccharides, polysaccharides, peptides, and mixtures thereof. More specifically, suitable polymers include poly(ethyleneglycol) (PEG), poly(propyleneglycol), poly(vinylpyrrolidone) (PVP), poly(hydroxyethylmethacrylate), poly(.epsilon.-caprolactone), poly(lactic acid), poly(glycolic acid), peptoids, oligocarbamates, oligoureas, and mixtures thereof. The peptides and unnatural stepwise oligomers may bear hydrophilic side chains such as PEG oligomers, PVP oligomers, monosaccharides, oligosaccharides, and cyclodextrins or those side chains comprising polar functional groups such as —OR (wherein R is hydrogen or an alkyl or aromatic group), —CONRR' (wherein R and R' are independently hydrogen or an alkyl or aromatic group), —NRR' (wherein R and R' are independently hydrogen or an alkyl or aromatic group), —NR(CNR'(NR"R'")) (wherein R, R', R", and R'" are independently hydrogen or an alkyl or aromatic group), —COOR (wherein R is a hydrogen or an alkyl or aromatic group), —SO3R (wherein R is a hydrogen or an alkyl or aromatic group), —P(O)(OR)(OR') (wherein R and R' are independently hydrogen or an alkyl or aromatic group), —NRR'R"(+) (wherein R, R', and R" are all alkyl or aromatic groups), and mixtures thereof. In some embodiments, the polymer is methoxy PEG amine. In some embodiments, the polymer is thiol PEG amine. As noted above, the hydrophilic polymer component B of the block co-polymer of the micelle orients toward the external aqueous environment, but may also interact significantly in a lateral fashion with the adjacent hydrophilic polymers, such that the micellar structure is stabilized.

The peptide component of the block co-polymer displayed on the surface of the micelles target the micelles to cells of interest. In some embodiments, the peptides target the micelles to colon, cervix, thyroid, brain, breast, ovary, prostate, liver, lung, esophagus, stomach, bladder, biliary tract, pancreas, oral cavity and/or skin cells of the patient. In some embodiments, the cells are dysplastic, early cancer and/or cancer cells. In some embodiments, the peptides target the micelles to CRC cells. In some embodiments, the peptide (in single letter amino acid code) is LTTHYKL (SEQ ID NO: 18). In some embodiments, the peptide is NGTTSSNNQLINENNIQN (SEQ ID NO: 1), EHMYN-TPHTYHTTMKNNK (SEQ ID NO: 2), QPIHPNNM (SEQ ID NO: 3), NKLAAALE (SEQ ID NO: 4), KNYKN (SEQ ID NO: 5), TNTHN (SEQ ID NO: 6), KHTNN (SEQ ID NO: 7), SILPYPY (SEQ ID NO: 8), KCCFPAQ (SEQ ID NO: 9), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 14), NFMESLPRLGMH (SEQ ID NO: 15), HYKL (SEQ ID NO: 16), AKPGYLS (SEQ ID NO: 17) or LTTHYKL (SEQ ID NO: 18). In some embodiments, the peptide is an EGFR-specific peptide QRHKPRE (SEQ ID NO: 19), HAHRSWS (SEQ ID NO: 20), YLTMPTP (SEQ ID NO: 21), TYPISFM (SEQ ID NO: 22), KLPGWSG (SEQ ID NO: 23), IQSPHFF (SEQ ID NO: 24), YSIPKSS (SEQ ID NO: 25), SHRNRPRNTQPS (SEQ ID NO: 26), NRHKPREKTFTD (SEQ ID NO: 27), TAV-PLKRSSVTI (SEQ ID NO: 28), GHTANRQPWPND (SEQ ID NO: 29), LSLTRTRHRNTR (SEQ ID NO: 30), RHRDTQNHRPTN (SEQ ID NO: 31), ARHRPKLPYTHT (SEQ ID NO: 32), KRPRTRNKDERR (SEQ ID NO: 33), SPMPQLSTLLTR (SEQ ID NO: 34) or NHVHRMHATPAY (SEQ ID NO: 35). In some embodiments, the peptide is a claudin-1 specific peptide RTSPSSR (SEQ ID NO: 36), HLQLQRL (SEQ ID NO: 37), IQTNPTM (SEQ ID NO: 38), RSLTQQT (SEQ ID NO: 39), SLQHLRS (SEQ ID NO: 40), IQLKINS (SEQ ID NO: 41), ITIRQHI (SEQ ID NO: 42), RRSNSQL (SEQ ID NO: 43), LNRIRRR (SEQ ID NO: 44), NNMKKIT (SEQ ID NO: 45), LQSLISK (SEQ ID NO: 46), IHTRRRK (SEQ ID NO: 47), RPNKPRI (SEQ ID NO: 48), RHRRSPI (SEQ ID NO: 49), ITLSITQ (SEQ ID NO: 50), KTQLMII (SEQ ID NO: 51), RPRQLQR (SEQ ID NO: 52), TRRHTII (SEQ ID NO: 53), RIIHKNM (SEQ ID NO: 54), LLTISPK (SEQ ID NO: 55), LLPMHMN (SEQ ID NO: 56), TSPMLSI (SEQ ID NO: 57) or LRNNIRH (SEQ ID NO: 58). In some embodiments, the peptide is a HER2-specific peptide KSPNPRF (SEQ ID NO: 59), RHPFPRF (SEQ ID NO: 60), RHPWPNR (SEQ ID NO: 61), RHPYPQR (SEQ ID NO: 62) or RKPFPRH (SEQ ID NO: 63). U.S. patent application Ser. No. 13/329,741; International Patent Application No. PCT/US2015/046314; U.S. Provisional Application No. 62/121,663; and U.S. Provisional Application No. 62/262,159 describing such peptides are hereby incorporated by reference (as is also noted in paragraph [146]).

Peptides contemplated herein include D and L forms, either purified or in a mixture of the two forms. Also contemplated by the present disclosure are peptides that compete with peptides of the invention for binding to colon cells.

It will be understood that peptides and linkers of the invention optionally incorporate modifications known in the art and that the location and number of such modifications are varied to achieve an optimal effect.

In some embodiments, the peptide is a peptide analog having a structure based on one of the peptides disclosed herein (the "parent peptide") but differs from the parent peptide in one or more respects. Accordingly, as appreciated by one of ordinary skill in the art, the teachings regarding the parent peptides provided herein may also be applicable to the peptide analogs.

In some embodiments, the peptide analog comprises the structure of a parent peptide, except that the peptide analog comprises one or more non-peptide bonds in place of peptide bond(s). In some embodiments, the peptide analog comprises in place of a peptide bond, an ester bond, an ether bond, a thioether bond, an amide bond, and the like. In some embodiments, the peptide analog is a depsipeptide comprising an ester linkage in place of a peptide bond.

In some embodiments, the peptide analog comprises the structure of a parent peptide described herein, except that the peptide analog comprises one or more amino acid substitutions, e.g., one or more conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative ammo acid substitution may be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

In some embodiments, the peptide analog comprises one or more synthetic amino acids, e.g., an amino acid non-native to a mammal. Synthetic amino acids include (β-alanine (β-Ala), N-α-methyl-alanine (Me-Ala), aminobutyric acid (Abu), γ-aminobutyric acid (γ-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe(4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (MeVal), and alkylated 3-mercaptopropionic acid.

In some embodiments, the peptide analog comprises one or more non-conservative amino acid substitutions and the peptide analog still functions to a similar extent, the same extent, or an improved extent as the parent peptide. In certain embodiments, the peptide analog comprising one or more non-conservative amino acid substitutions exhibits about the same or greater binding to target cells (including, but not limited to, dysplastic cells, early cancer cells and/or cancer cells) in comparison to the parent peptide.

In some embodiments, the peptide analog comprises one or more amino acid insertions or deletions, in comparison to the parent peptide described herein. In some embodiments, the peptide analog comprises an insertion of one or more amino acids in comparison to the parent peptide. In some embodiments, the peptide analog comprises a deletion of one or more amino acids in comparison to the parent peptide. In some embodiments, the peptide analog comprises an insertion of one or more amino acids at the N- or C-terminus in comparison to the parent peptide. In some embodiments, the peptide analog comprises a deletion of one or more amino acids at the N- or C-terminus in comparison to the parent peptide. In these embodiments, the peptide analog still exhibits about the same or greater binding to target cells (including, but not limited to, dysplastic cells, early cancer cells and/or cancer cells) in comparison to the parent peptide.

Micelles are prepared and loaded with a drug of interest by methods standard in the art. Generally, a disclosed block co-polymer in an aqueous media is mixed with the drug in organic solvent and the mixture is sonicated. The organic solvent is then removed. The resulting self-assembled micelles are separated from insoluble material. The micelles are sterilized by filtration using typical sterilization filters, for example, filters with 0.45-mm or 0.22-mm pores.

In some embodiments, the micelle has a hydrodynamic diameter in the range of from about 1 to about 100 nm. In some embodiments, the micelle has a hydrodynamic diameter in the range of about 5 to about 80 nm.

The terms "drug," "therapeutic compound," "active agent" and "pharmaceutically active agent" are used interchangeably herein to mean any compound useful for therapeutic, nutritional, or diagnostic purposes. Further, the term encompasses one or more of such compounds, or one or more of such compounds in combination with another active agent(s).

It will be appreciated by those skilled in the art that drugs can be used in the form of pharmaceutically acceptable salts, free bases, prodrugs (e.g., esters) or derivatives and, in the case of chirally active ingredients, one can use one or both optical isomers, geometric isomers and mixtures thereof including racemic mixtures.

The micelles of the disclosure are used to encapsulate a hydrophobic drug. In some embodiments, the drug is a drug used to treat cancer. In some embodiments, the drug is an mTOR inhibitor. In some embodiments, the drug is rapamycin. In some embodiments, the drug is doxorubicin. In some embodiments, the drug is paclitaxel. In some embodiments, the drug is cyclosporin A. In some embodiments, the drug is geldanamycin. In some embodiments, the drug is dipyridamole. In some embodiments, the drug is camptothecin.

Pharmaceutical compositions or "dosage forms" comprising the micelles carrying a drug are provided herein. The concentration of drug in a dosage form depends, of course, on the desired dosage of the active agent. It will be appreciated that the amount of a drug required for use in treatment will vary not only with the particular drug selected but also the nature of the condition for which treatment is required, and the desired dosage regimen, it being understood that extended or sustained release dosage forms such as those described herein are usually intended to reduce the number of dosages taken per day or to sustain a desired plasma level. Additionally, the necessity or desire for other components of the dosage form will serve to dictate the maximum percentage of drug. In general, however, the dosage form contemplated herein will contain anywhere from about 0.5% to about 90% by weight of the drug, from about 1 to about 50%, from about 7 to about 17%, or from about 1 to about 10%.

Micelles of the disclosure are formulated with pharmaceutically acceptable excipients such as carriers, solvents, stabilizers, adjuvants, diluents, etc., depending upon the particular mode of administration and dosage form. The compositions are generally formulated to achieve a physiologically compatible pH, and range from a pH of about 3 to a pH of about 11, or about pH 3 to about pH 7, depending on the formulation and route of administration. In alternative embodiments, the pH is adjusted to a range from about pH 5.0 to about pH 8. In various embodiments, the compositions comprise a therapeutically effective amount of at least one micelle described herein, together with one or more pharmaceutically acceptable excipients. Optionally, the compositions comprise a combination of the micelles described herein, or may include a second active ingredient useful in the treatment or prevention of bacterial growth (for example and without limitation, anti-bacterial or anti-microbial agents.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol) wetting or emulsifying agents, pH buffering substances, and the like.

The micelles are applicable to the delivery of any hydrophobic drug. In some embodiments of the present dosage forms, there may be more than one such hydrophobic drug, or such a drug in combination with any other agent, hydrophobic or not.

In another aspect, the invention provides a kit for administering a micelle described herein to a patient in need thereof, where the kit comprises a micelle, instructions for use of the micelle and a device for administering the micelle to the patient. In some embodiments, the micelles are lyophilized.

Administration and Treatment

In another aspect, the present invention provides methods of administering a dosage form containing the micelles disclosed herein to an animal, preferably a human. In some embodiments, the dosage forms described herein are administered by an oral route. In some embodiments, the dosage forms are administered by an i.v. route. The desired dose may conveniently be presented in a single dose or as divided dose administered at appropriate intervals, for example as two, three, four or more doses per day.

Dosages of the therapeutic moiety provided are administered as a dose measured in, for example, mg/kg. Contemplated mg/kg doses of the disclosed therapeutics include about 1 mg/kg to about 60 mg/kg. Specific ranges of doses in mg/kg include about 1 mg/kg to about 20 mg/kg, about 5 mg/kg to about 20 mg/kg, about 10 mg/kg to about 20 mg/kg, about 25 mg/kg to about 50 mg/kg, and about 30 mg/kg to about 60 mg/kg. In some embodiments the dose is 5 mg/kg. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

The methods contemplated herein comprise the step of administering an effective dose, or effective multiple doses, of a dosage form described herein to an animal (including a human being) in need thereof. If the dose is administered prior to development of a disorder/disease, the administration is prophylactic. If the dose is administered after the development of a disorder/disease, the administration is therapeutic. In embodiments of the invention, an "effective dose" is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. In some embodiments, the disease is pre-cancer (dysplasia). In some embodiments, the disease is early cancer. In some embodiments the disease is cancer. In some embodiments, the cancer is CRC.

Combination therapies are also contemplated by the invention. Combination as used herein includes simultaneous treatment or sequential treatments. Combinations of disclosed methods with standard medical treatments are specifically contemplated, as are combinations with novel therapies.

EXAMPLES

The invention will be more fully understood by reference to the following examples which detail exemplary embodiments of the invention. The examples demonstrate a dramatic therapeutic effect on colorectal adenomas in CPC; Apc mice systemically administered rapamycin encapsulated in micelles labeled with targeting peptides. The micelles were prepared by conjugating hydrophobic octadecyl lithocholate with hydrophilic PEG. Rapamycin is used as a model lipophilic drug that partitions spontaneously into the micelle core. This formulation produced comparable therapeutic effectiveness to free rapamycin, as shown by complete adenoma regression, with significantly less adverse systemic effects.

Materials and Methods Used in the Examples

Cells and Reagents

Human colorectal carcinoma cells (SW620, HT29, SW480, and DLD1), normal colonic cells (CCD841CON), and HEK293 cells were obtained from the ATCC (Manassas, Va.). Dulbecco's modified Eagle's medium (DMEM), Eagle's minimal essential medium (EMEM), McCoy's 5A medium, phosphate-buffered saline (PBS), and penicillin-streptomycin were obtained from GIBCO. Fetal bovine serum (FBS) was obtained from Invitrogen. SW620, SW480, DLD1, and HEK293 cells were grown in DMEM. HT29 cells were grown in McCoy's 5A. CCD841CON cells were grown in EMEM. Cells were maintained according to ATCC guidelines.

Lithocholic acid, octadecyl amine, N,N'-diisopropylcarbodiimde (DIC), N-(3-dimethylaminopropyl)-N'-ethylcarbodiimide HCl (EDC), N-hydroxysuccinimide (NHS), 4-(dimethylamino) pyridine (DMAP), N,N-diisopropylethylamine (DIEA), succinic anhydride, pyrene, coumarin 6, triton-X100, and 3-[4,5-dimethylthiazol-2-yl]-2,5 diphenyl tetrazolium bromide (MTT) were obtained from Sigma. Maleimidopropionic acid was obtained from Toronto Research Chemical Inc. Tris (2-carboxyethyl) phosphine HCl (TCEP) was obtained from Thermo Scientific. Rapamycin was purchased from LC Laboratories. Methoxy PEG$_{3K}$ amine and thiol PEG$_{3.5K}$ amine were obtained from JenKem Technology. Fmoc-amino acids, Boc amino acids, o-benzotriazole-N,N,N',N'-tetramethyluronium hexafluorophosphate (HBTU) and 1-Hydroxybenzotriazole (HOBt) were obtained from Aapptec and AnaSpect. Rink amide MBHA resin was obtained from Novabiochem. Tween-20 was purchased from Promega. Dialysis membranes with molecular weight cut off (MWCO) of 1 and 12-14 kDa were obtained from Spectrum Laboratories, Inc. Cy5.5 NHS ester was obtained from Lumiprobe. All reagents were used as received.

Animal Model 8-10 month old CPC; Apc mice genetically engineered with a Cre regulated somatic deletion in one Apc allele were used. These mice spontaneously produce adenomas in the distal colon that range in size from 2 to 4 mm in diameter at this age. Mice were cared for with approval of the University Committee for Use and Care of Animals (UCUCA) at the University of Michigan. Mice were housed in specific pathogen-free conditions and supplied water ad libitum throughout the study.

Selection of Peptide for Micelle Labeling

Our laboratory has previously identified a group of peptides that bind specifically to colonic adenomas in the CPC; Apc mouse. Peptides QPIFIPNNM (SEQ ID NO: 3), KCCFPAQ (SEQ ID NO: 9), LTTHYKL (SEQ ID NO: 18), and AKPGYLS (SEQ ID NO: 17) were identified using phage display technology. Peptides YTTTNAS (SEQ ID NO: 64) and DNEPIAQ (SEQ ID NO: 65) were included as controls. These peptides were identified based on an unbiased screen of cells and tissues to maximize specific binding in vivo. The peptides were labeled with Cy5.5 and injected via tail vein at a concentration of 200 µM in 1×PBS. The peptides were allowed to circulate for 1 hour to allow for non-specific binding to clear. The colon was rinsed again with tap water. Fluorescence images were then collected. A total of n=22 mice (n=59 adenomas) were studied. Fluorescence images for each adenoma were analyzed by defining a region of interest (ROI) around the adenoma and adjacent normal-appearing mucosa using ImageJ software. The mean values were calculated for each ROI, and the T/B ratio was determined. The mean T/B ratio for each peptide was calculated, and Kruskal-Wallis and Dunn's multiple comparison tests were used to determine statistical differences.

Selection of Peptide Density to Coat Micelle Surface

HT29 cells (5×10$^4$ cells/mL) were grown on gelatin coated cover slips up to ~80% confluence. Cells were washed with PBS, blocked with 0.5% bovine serum albumin (BSA) for 30 min at 4° C., and washed with PBS. Cells were incubated with coumarin-6 encapsulated micelles (1.3 mg/mL) with various LTT* peptide densities (0, 25, 50, and 75%) for 60 min at 4° C. Cells were washed with PBS three times, fixed with 4% paraformaldehyde (PFA) for 5 min, washed once with PBS, and then mounted on glass slides with Prolong Gold reagent containing DAPI. Fluorescence images were collected with FITC and DAPI filters on an Axioskop2 upright microscope (Carl Zeiss Microimaging, Inc). Fluorescence images were quantified with ImageJ software by averaging 3 images for each cell and peptide density. The florescence intensity from each image was normalized by number of cells using DAPI intensity.

NIR Peptide Synthesis for In Vivo Peptide Selection

A panel of peptides [QPIHPNNM-GGGSK (SEQ ID NO: 66), KCCFPAQ-GGGSK (SEQ ID NO: 67), LTTHYKL-GGGSK (SEQ ID NO: 68), AKPGYLS-GGGSK (SEQ ID NO: 69), YTTTNAS-GGGSK (SEQ ID NO: 70) and DNEPIAQGGGSK (SEQ ID NO: 71)] was synthesized for selection of micelle labeling using solid phase peptide synthesis with standard Fmoc chemistry[6] on a PS3 (Protein Technologies, Inc.) automatic peptide synthesizer. Cy5.5 NHS ester was conjugated at the C-terminus on the side chain of a lysine residue via the GGGSK (SEQ ID NO: 72) linker. Resins (~0.03 mmol) were swelled in DMF (1 mL). In a separate tube, Cy5.5 NHS ester (18 mg, 0.03 mmol) was dissolved in DMF (0.6 mL). ~23 µL of DIEA(46 µL, 0.26 mmol) was added to both tubes. Cy5.5 solution was added to the resins. The reaction was allowed to stir 2-3 days at RT. The resins were washed and cleaved. The resulting peptides were precipitated in cold diethyl ether. The peptides were then purified using a semi-preparative HPLC (Water Breeze HPLC) with water—acetonitrile gradient mobile phase containing 0.1% trifluoroacetic acid (TFA). The resulting peptides were lyophilized and characterized with an ESI mass spectrometer (Micromass LCT Time-of-Flight mass spectrometer with electrospray). Peptide purity was >95% on analytical HPLC.

Peptide Synthesis for Micelle Conjugation

The LTTHYKL-GGGSK (SEQ ID NO: 68) peptide was selected for micelle labeling, and synthesized as described above. A maleimide functional group was conjugated at the C-terminus on the side chain of a lysine residue via a GGGSK (SEQ ID NO: 72) linker. Briefly, LTT* resins (~0.06 mmol) were swelled in DMF (1.5 mL). In another tube, 3-maleimidopropionic acid (25 mg, 0.15 mmol) and HOBt (70 mg, 0.46 mmol) were dissolved in DMF (1 mL). DIC (70 µL, 0.45 mmol) was added and the solution mixture was added to resins after 10 min of activation. The reaction was allowed to stir overnight at RT. Resins were washed, cleaved, and the resulting peptide was precipitated in cold diethyl ether. The peptide was then purified using a semi-preparative HPLC (Water Breeze HPLC) and characterized with an ESI mass spectrometer (Micromass LCT Time-of-Flight mass spectrometer with electrospray). Peptide purity was >95% on analytical HPLC.

Synthesis of Micelles

Octadecyl Lithocholate

Lithocholic acid (1.5 g, 4 mmol) and HOBt (1.5 g, 10 mmol) were dissolved in N,N-dimethylformamide (DMF) (12 mL). DIC (1.5 mL, 10 mmol) was added. After 10 min for activation, octadecyl amine (0.9 g, 3.3 mmol) was added along with dichloromethane (DCM) 4 mL, and the reaction was allowed to stir overnight at room temperature (RT). The resulting product was filtered and vacuum dried (MW 628 Da).

Succinyl Octadecyl Lithocholate

Octadecyl lithocholate (573 mg, 0.91 mmol) was dissolved in anhydrous DCM (15 mL). Catalytic amount of DMAP was added. Succinic anhydride (90.9 mg, 0.91 mmol) and DIEA (950 µL, 5.45 mmol) were then added and the reaction was allowed to run overnight at RT. The solvent was evaporated under N2 and the resulting product was vacuum dried (MW 728 Da).

Pegylated Octadecyl Lithocholate

Succinyl octadecyl lithocholate (64.2 mg, 0.09 mmol) was dissolved in DCM 2.5 mL and DMF 1 mL. HOBt (41.3 mg, 0.27 mmol) was added, following by adding DIC (50 µL, 0.27 mmol). Methoxy PEG amine (143 mg, 0.05 mmol) was added after 10 min for activation. The reaction was allowed to stir overnight at 40° C. The solvent was partially removed under N2 and the resulting product was precipitated in cold diethyl ether, centrifuged, and vacuum dried. Succinyl octadecyl lithocholate was conjugated with thiol PEG amine in the same manner.

Micelle Platform for Targeted Drug Delivery

Maleimide Peptide and Thiol Pegylated Octadecyl Lithocholate Conjugation

Thiol pegylated octadecyl lithocholate (74.8 mg, 0.02 mmol) and TCEP (9.68 mg, 0.03 mmol) were dissolved in phosphate buffer pH 8.0 (15 mL). Maleimide peptide (0.02 mmol) was added and the reaction was allowed to run overnight at RT. The resulting product was dialyzed against three changes of water (MWCO 1 kDa) and lyophilized.

Micelle Preparation

The micelles were prepared by dissolving pegylated octadecyl lithocholate and/or LTT* pegylated octadecyl lithocholate in PBS. Polymers were sonicated ~30 min or until fully dispersed. Rapamycin (18 mg/mL) or coumarin-6 (0.25 mg/mL) ethanolic stock solution was added to the polymer solution. The solution was sonicated for 5 min. The organic solvent was removed by purging with N2. After removing the organic solvent, the micelle solution was centrifuged at 8000 rpm for 10 min to remove insoluble material. Rapamycin or coumarin-6 micelles in supernatant were separated. For the cell staining, cytotoxicity and in vivo targeted therapy experiments, 0.35, 0.67, and 1.73 mM of polymer was used, respectively.

Micelle Platform Characterization

Nuclear Magnetic Resonance (NMR) Spectroscopy $^1$H NMR spectra were recorded on a Varian MR400 spectrometer to monitor changes in chemical structure of polymer conjugates. The conversion of hydroxyl group of octadecyl lithocholate to carboxyl group on succinyl octadecyl lithocholate was proven by the disappearance of the OH signal at 3.6 ppm. Octadecyl lithocholate: C—H$_2$ methylene (1.3 ppm), C—H cyclopentane, cyclohexane (1.2-1.5, 3.2 ppm), O—H (3.6 ppm), N—H (8.0 ppm). Succinyl octadecyl lithocholate: C—H$_2$ methylene (1.3, 2.5-2.6 ppm), C—H cyclopentane, cyclohexane (1.2-1.5, 3.2 ppm), N—H (8.0 ppm).

Fourier Transform Infrared (FTIR) Spectrometer

FTIR spectra were recorded on a Perkin-Elmer FT-IR spectrometer (Spectrum BX) to monitor changes in chemical structure of polymer conjugates. Samples were prepared in potassium bromide (KBr) discs and spectra were recorded in the range of 4000-400 cm$^{-1}$. The conversion of hydroxyl group of octadecyl lithocholate to carboxyl group on succinyl octadecyl lithocholate was confirmed by the disappearance of vibration of hydroxyl group (O—H) ~3400 cm$^{-1}$. The product also had a new peak at 1734 cm suggesting the formation of ester carbonyl group. Octadecyl lithocholate: C=O(1656 cm$^{-1}$), C—H (2851, 2922 cm$^{-1}$), O—H (3340, 3420 cm$^{-1}$). Succinyl octadecyl lithocholate: C=O (1656, 1734 cm$^{-1}$), C—O (2362 cm$^{-1}$), C—H (2850, 2926 cm$^{-1}$).

Micelle Characterization

Dynamic Light Scattering (DLS)

Hydrodynamic diameters and surface charges of micelles were determined on a Mavern nanosizer (Nano-ZS90) with a 4 mW linear polarized laser (633 nm He—Ne). Samples were studied at 25° C. and in 10 mm diameter polystyrene cells. The hydrodynamic diameters were calculated from the Stoked-Einstein equation. Measurements were made in triplicate with independently prepared samples, and variability was reported as ±standard deviation.

Transmission Electron Microscopy (TEM)

TEM images were obtained on a Philips CM-100 transmission electron microscope. Samples were prepared onto copper grids with 1% uranyl acetate (negative staining).

Critical Micelle Concentration (CMC)

Micelles form spontaneously at the critical micelle concentration (CMC). Pyrene was dissolved in acetone (24 mM) and aliquots of stock solution were added to 1.5 mL eppendorf tubes to provide a final pyrene concentration of 6 µM. Acetone was evaporated and replaced with LTT* and plain micelles prepared with serial dilution (0.3-544 µM). Solutions were incubated at 55° C. overnight and left at RT for 3 hours prior to the experiment. We measured the fluorescence intensity of pyrene at $I_1$=371 nm and $I_3$=383 nm over a range of concentrations of LTT* and plain micelles on a Fluoromax-2 fluorimeter.[7] The intensity ratios of $I_1$ to $I_3$ were plotted as a function of logarithm of micelle concentration (log µM). The CMC value was taken from the intersection of the tangent to the curve at the inflection with the horizontal tangent through the points at concentrations.[8]

Entrapment Efficiency (EE)

The amount of rapamycin was determined by analytical HPLC (Water Breeze HPLC) equipped with a UV detector, with a Water C18 (150×1.5 mm, 5 µm) column. Detection was set at wavelength of 276 nm. Mobile phase A was 0.1% glacial acetic acid in water and mobile phase B was methanol. Linear gradient elution was carried out from 75% of B to 100% of B over 10 min at a flow rate of 1 mL/min. Column temperature was at ambient temperature. One hundred microliters of micelle solution was diluted with equal volume of 75% methanol in water prior to injection. The entrapment efficiency (% EE) was calculated according to the following equation:

$$\text{Entrapment efficiency }(\%EE) = \frac{\text{amount of encapsulated } rapamycin\ (\mu g) \text{ in } micelles}{\text{amount of added } rapamycin\ (\mu g) \text{ during formulation}} \times 100.$$

Release Study

Release experiments were based on the methodology of Forrest et al with slight modification.[9] Micelle solutions were prepared at 1.73 mM. Rapamycin was encapsulated ~12% (w/w) in micelles, and 8 mL of each solution was transferred into 12,000 Da MWCO dialysis bag (Spectrum laboratories Inc.) (n=3). Dialysis bags were placed in PBS, and the temperature was controlled at 37° C. At fixed time points, aliquots were taken, and drug concentrations were measured by reverse phase HPLC. Release medium (PBS) was refreshed every 2 hours. The nature of drug release behavior from micelle was investigated by an established exponential expression, $$\frac{M_t}{M_\infty} = kt^n,$$

where $M_t$ and $M_\infty$ are the absolute cumulative amount of drug released at time t and infinite time, respectively. The correlation coefficient ($R^2$) of each formulation was quantified from a plot of log ($M_t/M_\infty$) against log(t) for rapamycin release from micelles at various time points.

Chemical Stability

Chemical stability of micelles was evaluated over a 22 day study. Samples were prepared at 1.73 mM with rapamycin ~12% (w/w) in micelles, aliquoted in separated tubes and kept at 2-8° C. At each time point, sample tubes were brought to RT. The sample was diluted, and drug concentrations were assayed by reverse phase HPLC, as described in methods for % EE determination.

Specific Binding of Micelles to Surface of Cell Panel

SW620, HT29, SW480, DLD1, and CCD841CON cells (5×10⁴ cells/mL) were grown on gelatin coated cover slips up to ~80% confluence. The cells were washed with PBS, blocked with 0.5% bovine serum albumin (BSA) for 30 min at 4° C., and washed with PBS. The cells were incubated with coumarin-6 encapsulated micelles (1.3 mg/mL) that have 50% LTT* targeting peptide density for 60 min at 4° C. Cells were washed with PBS three times, fixed with 4% paraformaldehyde (PFA) for 5 min, once with PBS, and then mounted on glass slides with Prolong Gold reagent containing DAPI. Fluorescence images were collected on a Leica Inverted SP5X Confocal Microscope System. Fluorescence images were quantified with Matlab software by averaging 3 images for each cell. The florescence intensity from each image was normalized by number of cells using gray scale value of DAPI intensity.

Competitive Binding Assay

Specific binding of LTT*-labeled coumarin-6 micelles was validated on competitive inhibition with unlabeled LTT* peptide. This experiment was performed at the same time as that for specific cell surface binding. SW620, HT29, SW480, DLD1, and CCD841CON cells were prepared, as described above. Unlabeled LTT* peptides at 50 and 250 µM were incubated for 30 min at 4° C. Cells were then incubated with LTT*-labeled coumarin-6 encapsulated micelles (1.3 mg/mL) for 60 min at 4° C. The cells were washed with PBS three times, fixed with 4% paraformaldehyde (PFA) for 5 min, washed once with PBS, and then mounted on glass slides with Prolong Gold reagent containing DAPI. Fluorescence images were collected on a Leica Inverted SP5X Confocal Microscope System. Fluorescence images were quantified with Matlab software by averaging 3 images for each cell and unlabeled peptide concentration. The florescence intensity from each image was normalized by number of cells using gray scale value of DAPI intensity.

Endoscopy Calibration

Endoscopy calibration was based on the methodology described previously with slight modification.[21] A small animal endoscope with a 0° viewing angle and 1.5-mm outer diameter (Karl Storz Veterinary Endoscopy, Goleta, Calif.) was used to identify and measure all adenomas. An image of a grid with 1×1 mm² squares was captured with the endoscope at various distances away, in 0.5-mm increments, using the endoscope and a movable stage equipped with a digital caliper. At given distances from endoscope tip to the grid, surface area of grid images was calculated using ImageJ software. A relationship between surface area and distances was set and validated, with level of accuracy 96%. This relationship was used to quantify adenoma surface area from adenoma images with known distance from endoscope tip to adenomas.

In Vivo Imaging of Colonic Adenomas in CPC; Apc Mice

We performed in vivo imaging of colon in CPC; Apc mice to select the peptide to label the micelles. The mice were placed on a heat pad. Anesthesia was induced and sedation was maintained using inhaled isoflurane mixed with oxygen via a nose cone at a dose of 4% and 1.5%, respectively, and a flow rate of 0.5 L/min. A small animal endoscope (Karl Storz Veterinary Endoscopy) was used to visualize the colon[7]. A stage was used to adjust the position of the mouse and to manipulate the endo scope and calipers. The distal tip of the endoscope was inserted rectally, and advanced. Debris was rinsed away with water. The colon was insufflated with air to keep the lumen open. Adenomas with diameter of >1.5 mm were identified, and the location from the anus was recorded. A distance of 0 mm was defined when the endoscope tip touched the adenoma. The distance of the endoscope tip to the adenoma was recorded during withdrawal using a gauge. Videos were recorded, and individual images were exported using Axiovision Lite software. The surface area of the adenoma was quantified using established relationship between distance of endoscope tip to the adenoma and surface area of a grid with 1×1 mm² squares.

Adenoma Regression with Targeted Rapamycin Micelle Therapy

CPC; Apc mice were randomly divided into four treatment groups (n=6, 6, 6, and 7, respectively): 1) normal saline solution (NSS), 2) free rapamycin, 3) unlabeled (plain) rapamycin micelles, and 4) LTT*-labeled rapamycin micelles. The number of mice (number of adenomas) at the end of the study were n=5 (20), 6 (24), 5 (22), and 7 (21), respectively. Two mice (one in NSS group and one in unlabeled (plain) rapamycin micelle group) died from unexplained cause. Mice in the treatment groups were given NSS, free rapamycin, plain rapamycin micelles, and LTT*-labeled rapamycin micelles at a dose of 5 mg/kg through a daily intraperitoneal (i.p.) injection for 35 days. Mice underwent endoscopy every ~4 days to monitor adenoma regression and were weighed every 2 days for 5 weeks. A total of n=230 colonoscopy examinations was performed.

Safety of Micelles
Blood Chemistries

After completion of therapy, the CPC; Apc mice were euthanized by carbon dioxide ($CO_2$) overdose. Blood was collected immediately by cardiac puncture, per UCUCA guidelines, and submitted to the Unit for Laboratory Animal Medicine (ULAM) Pathology Cores for Animal Research (PCAR) for evaluation of chemistries.

Necropsy

All tissues (heart, spleen, kidney, liver, and colon) were fixed in phosphate-buffered formalin for 24 h, paraffin-embedded, and cut in 10 μm sections. Routine histology (H&E) was performed. Renal toxicity was assessed after completion of therapy. Histology (H&E) from representative murine kidney sections (n=4) from the different treatment groups were evaluated for tubules with vacuoles on five random fields (400× magnification) for each specimen.

Cytotoxicity

Cytotoxicity was determined by measuring growth inhibition for a panel of cells (SW620, HT29, SW480, DLD1, CCD841CON, and HEK393) on an MTT assay. Cell viability was calculated based on a comparison of untreated cells and those treated with free rapamycin and with plain and LTT*-labeled rapamycin micelles under the same conditions. The panel of cells were harvested and seeded at a density of $5 \times 10^3$ cells/well in 96-well plates. Cells were cultured for 24 h prior to adding rapamycin micelles in serial dilution. Free rapamycin at equivalent doses was incubated with cells in the same manner. After 1 day for incubation in culture medium without phenol red, the medium was removed, cells were washed twice with PBS, and MTT solution (100 μL, 0.5 mg/mL) was added to each well. After an additional 4 h for incubation, MTT solution was removed. Formazan crystals produced by live cells were solubilized in DMSO and the absorbance was measured at 570 nm (test) and 630 nm (reference) using a microplate reader. Cytotoxicity of tested substance was presented as the half maximal inhibitory concentration ($IC_{50}$). At the concentration, the test substance inhibits cell viability by 50%.

Immunohistochemistry (IHC) of Adenoma Regression

Immunohistochemistry was performed using the following dilutions of primary antibodies: mouse anti-total ß-catenin (1:600, BD Transduction Laboratories), rabbit anti-Ki67 (1:500, Pierce), and rabbit anti-phospho-S6 ($Ser^{235/236}$, 1:150, clone 91B2, Cell Signaling Technology) and developed with DAB (3,3' diaminobenzidine) substrate. The integrated optical density was measured from randomly placed IHC-positive areas of cells from 3 boxes ($20 \times 20$ μm$^2$) for each section using custom Matlab software (MathWorks) to quantify IHC staining[8]. The mean result was determined by averaging 7 images per antibody for each treatment group.

Statistical Analysis

A linear mixed effects regression models was used to assess efficacy and toxicity. An interaction between treatment groups and time (days) was estimated in the model to compare adenoma regression rates among the different rapamycin formulations. The model has two random effects to incorporate a correlation between data measured on the same adenoma and a correlation between adenomas found within the same animal. For weights, only one random effect was used to model the correlation between data from the same animal. A comparison was considered significant if P<0.01 to adjust for multiple comparisons. All analyses were performed using SAS ver 9.3. Unless stated otherwise, all data were tested for normality. A one-way ANOVA or non-parametric Kruskal-Wallis was used to determined statistical significance for comparisons among more than 2 groups. If there was at least one difference between treatment groups, multiple comparisons were used to search for pairwise differences. Tukey's multiple comparison test was used to find pairwise differences after ANOVA analysis. Dunn's multiple comparison test was used to find pairwise differences after Kruskal-Wallis. All statistical computations were processed using either Graphpad Prism or Matlab software.

Example 1

Selection of Peptide for Micelle Labeling

Figure 6:
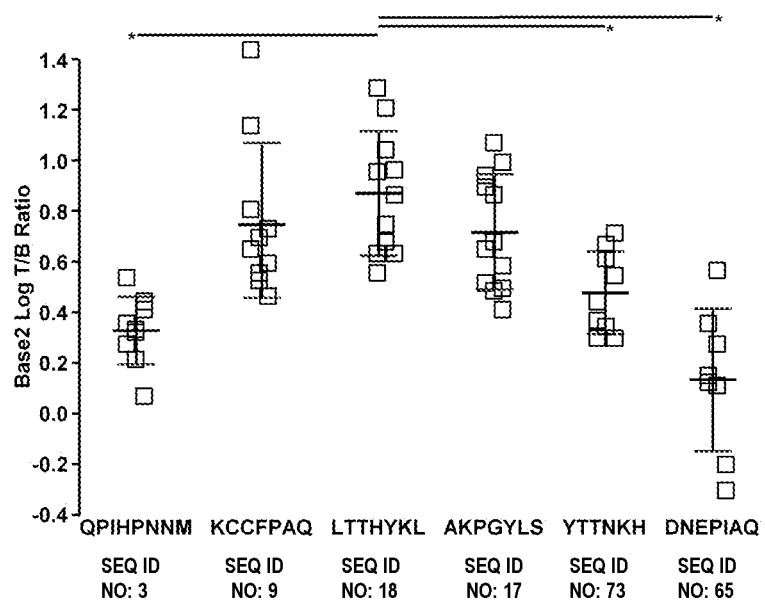
FIG. 6 relates to the selection of an exemplary peptide for micelle labeling. A panel of peptides were evaluated in vivo on fluorescence endoscopy for binding to spontaneous colonic adenomas in a CPC; Apc mouse model of spontaneous CRC, including QPI* (n=3 mice, 9 adenomas), KCC* (n=5 mice, 10 adenomas), LTT* (n=4 mice, 11 adenomas), AKP* (n=3 mice, 12 adenomas), YTT* (n=4 mice, 9 adenomas), and DNE* (n=3 mice, 8 adenomas). The LTT* peptide showed strongest binding, P<0.05 by Kruskal-Wallis test and Dunn's multiple comparison test. Base 2 log of T/B ratios shown.

On endoscopy, we measured in vivo fluorescence intensities from binding of a panel of Cy5.5-labeled peptides administered intravenously to colonic adenomas and adjacent normal appearing mucosa. The target-to-background (T/B) ratios are shown, FIG. 6. The highest mean value was measured for the peptide LTTHYKL (SEQ ID NO: 18), hereafter LTT*, which was chosen to label the micelles. The result was significantly greater than that of other peptides, including QPIHPNNM (SEQ ID NO: 3), YTTNKH (SEQ ID NO: 64), and DNEPIAQ (SEQ ID NO: 65), and nonsignificantly greater than that of KCCFPAQ (SEQ ID NO: 9) and AKPGYLS (SEQ ID NO: 17), *P<0.05 by Kruskal-Wallis test and Dunn's multiple comparison test.

Example 2

Selection of Peptide Density to Coat Micelle Surface

Figure 7:
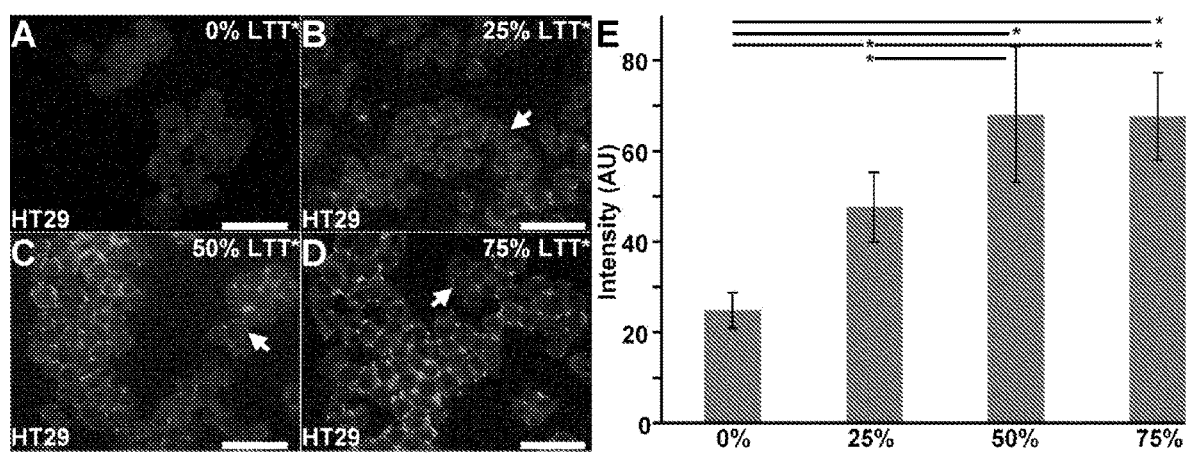
FIG. 7 relates to the selection of optimal peptide density to coat micelle surfaces. Micelles encapsulating coumarin-6 were labeled with LTT* peptide with mean surface densities of A) 0%, B) 25%, C) 50%, and D) 75%. E) Quantified fluorescence intensities on LTT*-labeled micelles binding to surface of HT29 cells on microscopy are shown. The mean fluorescence intensity for 50% LTT* peptide is significantly greater than that for 0% and 25% and non-significantly greater than that for 75%, *P<0.05 by Kruskal-Wallis test.

Micelles that encapsulated coumarin-6 were labeled with LTT* peptide covering an average surface density that included 0%, 25%, 50% and 75%. On microscopy, micelles bind to the surface of HT29 cells (arrows), FIG. 7A-D. The intensity of micelles coated with 50% LTT* was significantly greater than that for 0 and 25% and non-significantly greater than that for 75%, *P<0.05 by Kruskal-Wallis test, FIG. 7E. No significant improvement was found at increased density of 75%. Therefore, we labeled the micelles with 50% peptide density. This result can be explained by a multivalency effect whereby increased ligand density improves the likelihood of nanoparticle interaction with cell surface targets[10].

Example 3

Micelle Platform for Targeted Drug Delivery

We assembled a hydrophobic section of octadecyl lithocholate (blue) with hydrophilic polyethylene glycol (PEG, black) and LTT* peptide (red) at 50% density, FIG. 1A. Micelles formed by self-assembly from intermolecular forces aggregating the individual components in a predetermined fashion. We prepared micelles with either 50% LTT* and no peptide (plain) for control. On transmission electron microscopy (TEM), the LTT* and plain micelles (arrows) form a spherical geometry, scale bar 200 nm, FIG. 1B, C.

Example 4

Micelle Characterization

Figure 2:
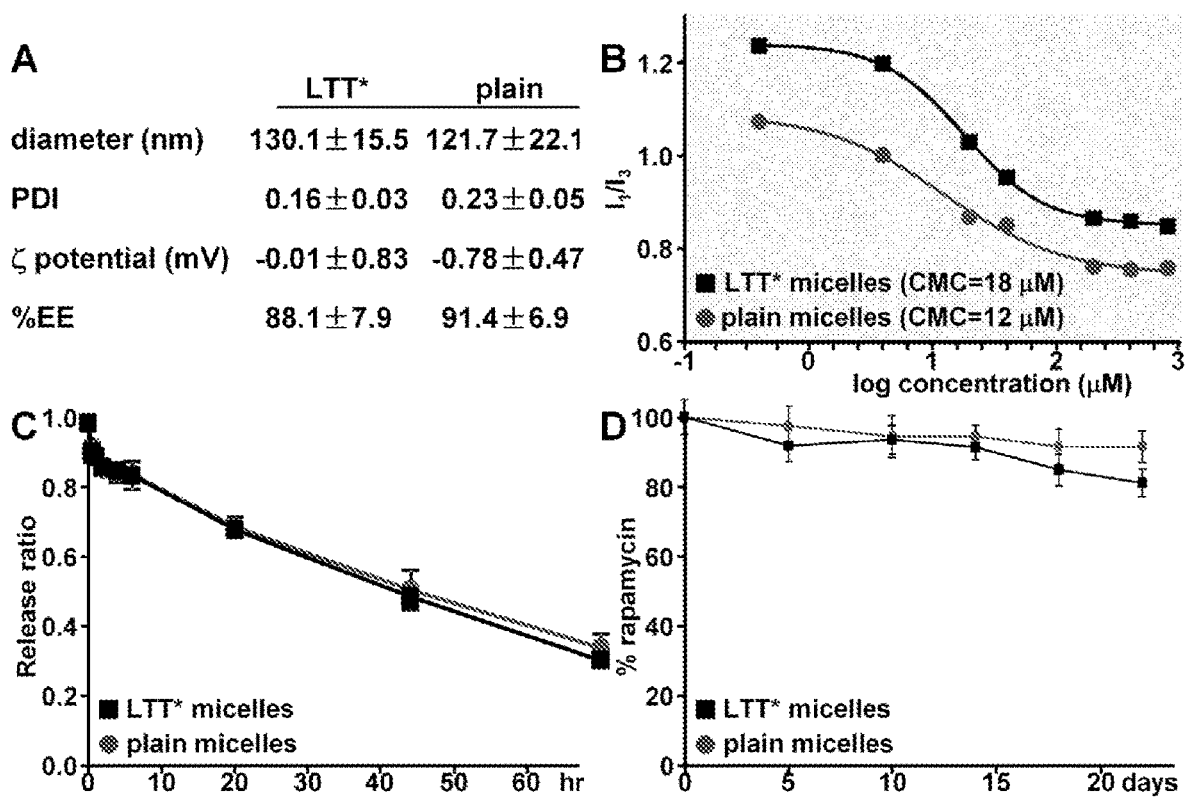
FIG. 2 relates to the micelle characterization. A) Parameters for LTT*-labeled and plain rapamycin micelles, including diameter on dynamic light scattering (DLS), polydispersity index (PDI), zeta (ζ) potential (surface charge), and rapamycin entrapment efficiency (% EE). B) The ratio of fluorescence intensities at I1=371 nm and I3=383 nm from pyrene mixed with LTT*-labeled and plain rapamycin micelles were measured to determine a critical micelle concentration (CMC) of 18 and 12 µM, respectively. C) LTT*-labeled and plain micelles provide a sustained release ratio for rapamycin over time with a half-life of ~44 h. D) LTT*-labeled and plain micelles retained 81.2% and 91.5% of the encapsulated rapamycin after 22 days.

We measured the hydrodynamic size of the rapamycin micelles on dynamic light scattering (DLS), and found a non-significant difference of 130.1±15.5 and 121.7±22.1 nm for LTT*-labeled and plain rapamycin micelles, respectively, P=0.62 by unpaired t-test, FIG. 2A. The size of the micelles measured was consistent with that seen on TEM. Both micelles had a polydispersity index (PDI) of ~0.2. This estimate of size distribution shows that the micelles were relatively monodispersed. The LTT*-labeled and plain rapamycin micelles had a slightly negative mean surface charge (zeta potential) of −0.01±0.83 and −0.78±0.47, respectively, and showed a non-significant difference in entrapment efficiency (% EE) for rapamycin of 88.1±7.9% and 91.4±6.9% (~13.8% and 15.8% w/w), P=0.61 by unpaired t-test, respectively. We measured a rapamycin concentration that ranged from 990 to 1005 μg/mL in micelle solution, resulting in a ~380-fold improvement in solubility compared to free rapamycin in water (2.6 μg/mL). We measured a critical micelle concentration (CMC) of 18 and 12 μM for LTT* and plain micelles, respectively, on fluorescence probe studies using pyrene, FIG. 2B. At the CMC, micelles form spontaneously and solubilize hydrophobic substances in water. Both LTT* and plain micelles showed a sustained release ratio of rapamycin over time with a halflife of ~44 h, FIG. 2C. Rapamycin release can be described by Fickian diffusion from a sphere[9], $R^2$=0.9488 and 0.9674, for LTT* and plain micelles, respectively. There was no burst release observed, suggesting that the rapamycin molecules partition predominantly in the micelle core. Chemical stability was assessed at 4° C. on reverse phase HPLC.LTT* and plain micelles were found to be stable up to 22 days with a high percentage of rapamycin retention, 81.2% and 91.5%, respectively, FIG. 2D.

Example 5

Specific Binding of Micelles to Surface of Cell Panel

Figure 8:
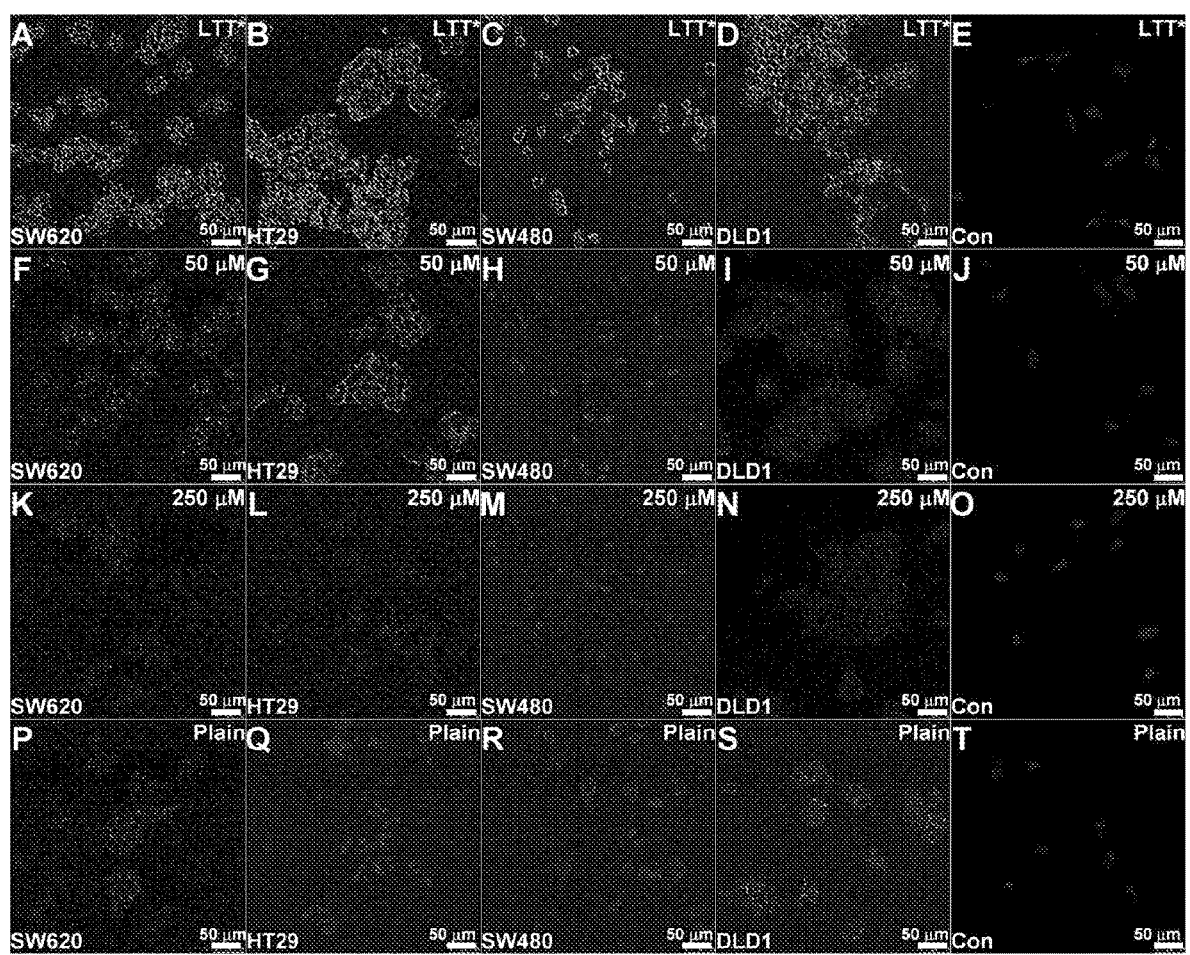
FIG. 8 relates to the specific binding of micelles to a cell panel. A-D) LTT*-labeled micelles encapsulating coumarin-6 show strong binding to panel of human colorectal cancer cells, including SW620, HT29, SW480, DLD1, and E) minimal binding to normal human colon CCD841CON (control) cells. Addition of free LTT* peptide at F-J) 50 and K-O) 250 µM demonstrates a concentration-dependent reduction in signal. P-T) Plain micelles show minimal binding to all cells.

We validated specific binding of LTT*-labeled rapamycin micelles encapsulating the fluorophore coumarin-6 to a panel of human CRC cells, including SW620, HT29, SW480, and DLD1, FIG. 8. On confocal microscopy, strong binding was observed to the surface of all cells, FIG. 8A-D. Minimal signal was observed for normal human colonic CCD841CON (control) cells, FIG. 8E. Free LTT* peptide at concentrations of 50 μM, FIG. 8F-J, and 250 μM, FIG. 8K-O, was added to compete with the LTT*-labeled rapamycin micelles containing coumarin-6 for binding.

Figure 9:
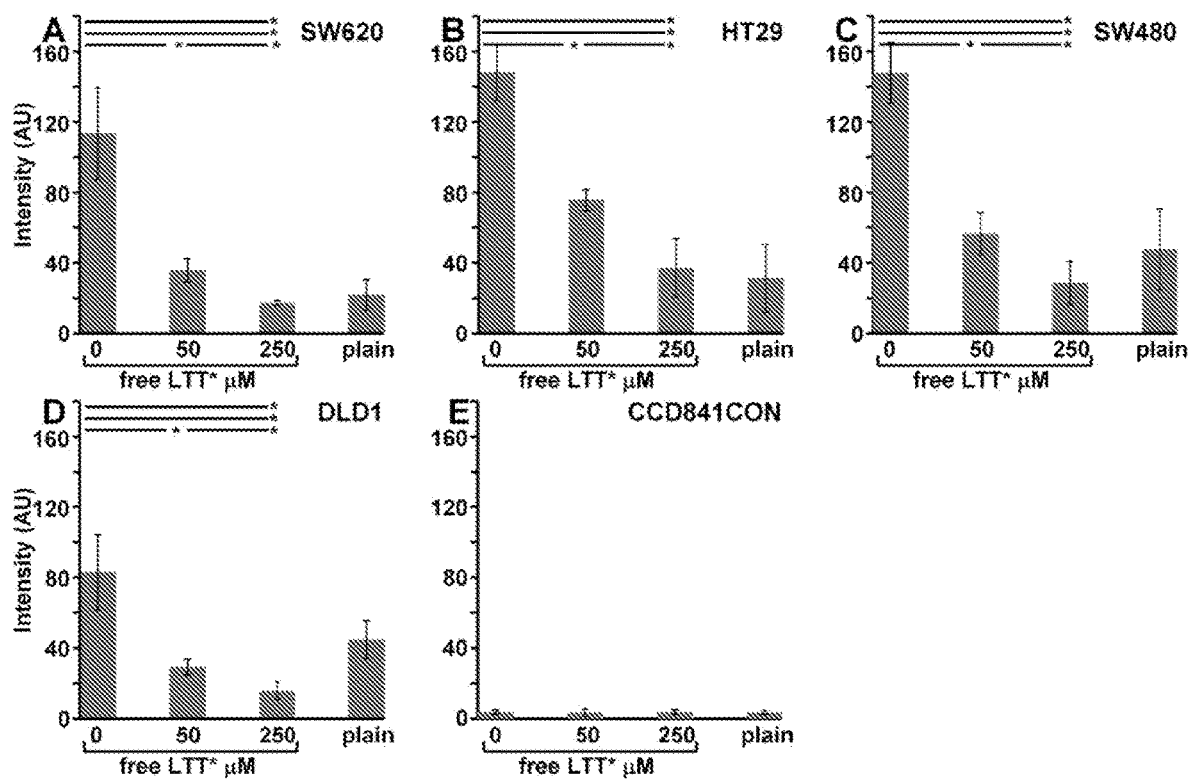
FIG. 9 relates to quantified fluorescence intensities on competitive inhibition with free peptide. Binding of LTT*-labeled micelles encapsulating coumarin-6 to human colorectal cancer cells, including A) SW620, B) HT29, C) SW480, and D) DLD1, shows concentration-dependent reduction in intensity with addition of free LTT* peptide, *P<0.05 by ANOVA. E) Minimal signal is seen for normal colon CCD841CON (control) cells. Minimal signal is seen with plain micelles for all cells.

Concentration-dependent reduction in signal was observed, FIG. 9. This result shows that the peptides rather than micelles mediate binding to the cell surface. Minimal signal was observed for plain rapamycin micelles (control), FIG. 8P-T.

Example 6

Adenoma Regression with Targeted Rapamycin Micelle Therapy

Figure 3:
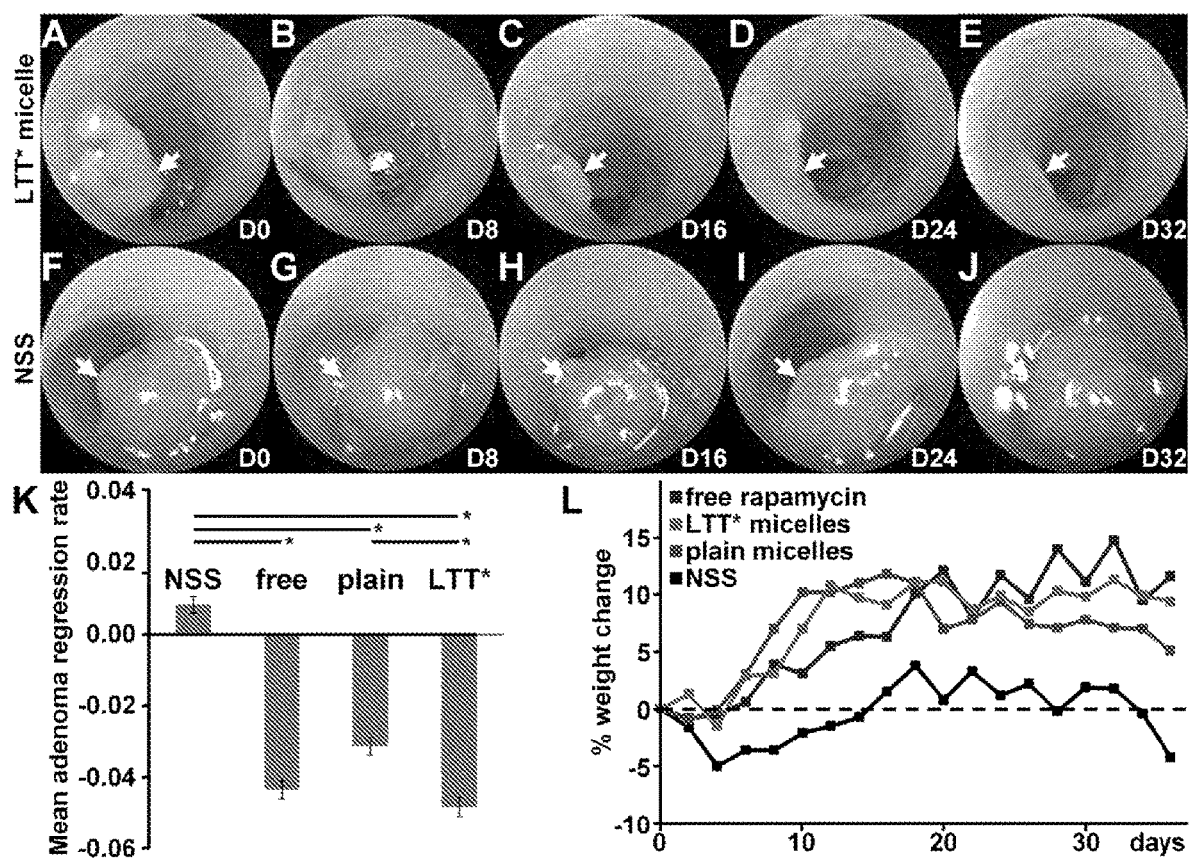
FIG. 3 shows adenoma regression with targeted rapamycin micelle therapy. In vivo images collected with white light endoscopy on days 0, 8, 16, 24, and 32 in CPC; Apc mice show A-E) rapid regression of colonic adenoma (arrow) with LTT*-labeled rapamycin micelle therapy. F-J) No regression was seen with no therapy, NSS (control). K) Relative tumor surface area (%) was monitored over time. L) The mean adenoma regression rate for LTT*-labeled rapamycin micelles was significantly greater than that for plain rapamycin micelles and NSS, and non-significantly greater than that of free rapamycin, *P<0.01 on linear mixed effects regression analysis. Results are from mice treated with NSS (n=5 mice, 20 adenomas), free rapamycin (n=6 mice, 24 adenomas), plain rapamycin micelles (n=5 mice, 22 adenomas), and LTT*-labeled rapamycin micelles (n=7 mice, 21 adenomas).

Groups of tumor-bearing mice were treated with free rapamycin, LTT*-labeled rapamycin micelles and plain rapamycin micelles via intraperitoneal injection for 35 days and with normal saline solution (NSS). On endoscopy, we observed rapid regression of large (2-4 mm) colonic adenomas (arrows) in response to therapy with LTT*-labeled rapamycin micelles over a 5-week period, FIG. 3A-E. In absence of therapy (NSS), no regression was observed, FIG. 3F-J. The mean regression rate for adenoma treated with LTT*-labeled rapamycin micelles was significantly greater than that for plain rapamycin micelles and NSS, and non-significantly greater than that for free rapamycin, *P<0.01 on linear mixed effects regression analysis, FIG. 3L. Many of the treated adenomas reverted to completely normal histology, FIG. 5D. While both labeled and unlabeled micelles can reach the tumor via an enhanced permeability and retention (EPR) effect, the presence of targeting ligands can increase therapeutic efficacy by mediating micelle internalization in tumor cells[10]. Mice treated with LTT*-labeled rapamycin micelles and free rapamycin gained more weight than mice that received no treatment (NSS) and plain rapamycin micelles, FIG. S6. All mice that received some form of rapamycin therapy showed improvement in physical signs, including greater activity, less rectal bleeding, and shinier hair, within ~1-2 weeks. In vivo monitoring was performed on repetitive endoscopic imaging over 5 weeks of therapy, FIG. 3.

Example 7

Safety of Micelles
Blood Chemistries

Figure 10:
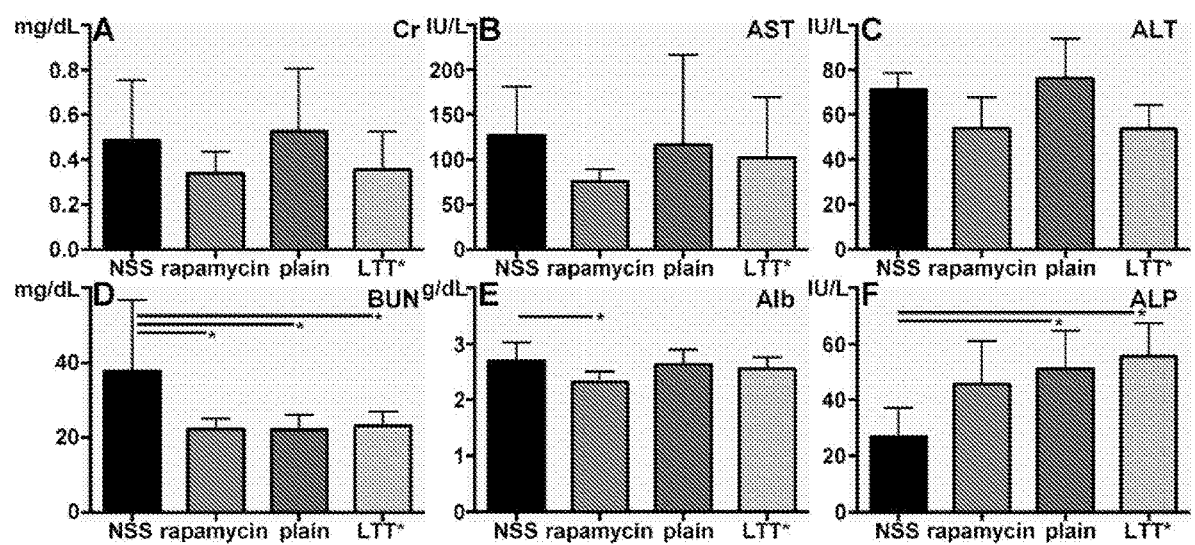
FIG. 10 relates to the toxicity profile of rapamycin encapsulated micelles. Mean(±std) blood chemistries from CPC; Apc mice after treatment with rapamycin formulations: A) creatinine (Cr), B) aspartate aminotransferase (AST), C) alanine aminotransferase (ALT), D) blood urea nitrogen (BUN), E) albumin (ALB), and F) alkaline phosphatase (ALP). ALP showed slight elevation for plain and LTT*-labeled micelles, *P<0.05 by ANOVA, however, these values fell in the normal range of ALP (65.5-364.2 U/L) for mice.

Labs performed on blood obtained from euthanized CPC; Apc mice after completion of rapamycin therapy are shown, FIG. 10. Although a significant elevation in alkaline phosphatase (ALP) was seen with the LTT*-labeled and plain rapamycin micelles compared to NSS, *P<0.05 by Kruskal-Wallis test, these values fell within the normal range (65.5-364.2 U/L) of ALP for mice.

Necropsy

Figure 4:
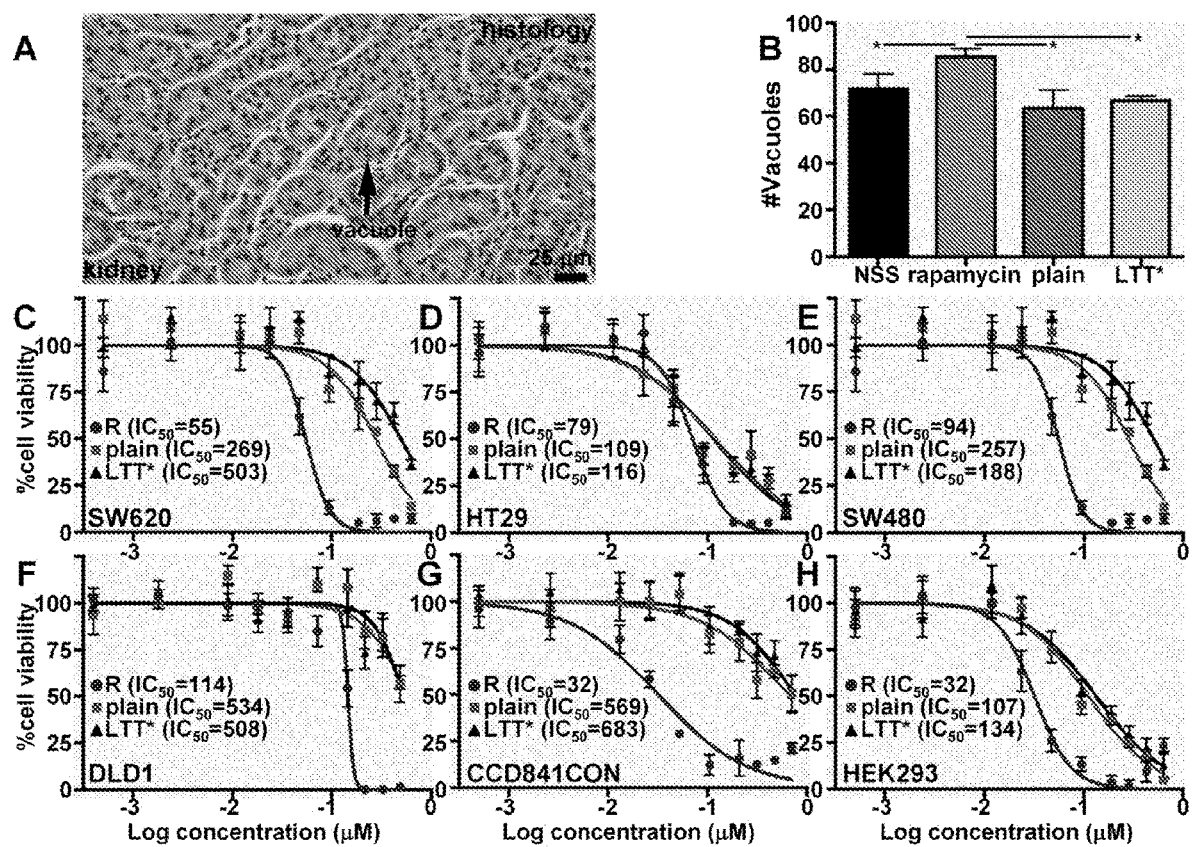
FIG. 4 relates to the safety of micelles. A) Renal toxicity was assessed on number of vacuolated renal tubules (arrow) seen on histology (H&E). B) Significantly fewer vacuoles were seen on histology in mice treated with plain and LTT*-labeled rapamycin micelles compared to those treated with free rapamycin, *P<0.05 by ANOVA. C) Cytotoxicity assay on cell panel shows that rapamycin encapsulated in either LTT*-labeled or plain rapamycin micelles resulted in significantly higher $IC_{50}$ compared to that for free rapamycin (R).

The CPC; Apc mice were euthanized after completion of therapy for necropsy, including examination of the heart, spleen, kidney, liver, and colon. Evidence for renal toxicity was assessed on histology (H&E) by counting the number of vacuolated tubules (arrow) per high-power field at 400× magnification, FIG. 4A. We observed significantly reduced renal toxicity in mice treated with rapamycin encapsulated in micelles by comparison to that with free drug. Mice treated with free rapamycin were found to have a significantly greater number of vacuoles per high-power field than mice treated with either LTT*-labeled or plain rapamycin micelles and untreated control mice (NSS), *P<0.05 by ANOVA, FIG. 4B. Both peptide-labeled and unlabeled micelles showed significantly fewer vacuolated tubules than that for free rapamycin in kidney on necropsy. Rapamycin therapy is associated with renal toxicity, including distal magnesium wasting, tubular collapse, vacuolization and nephrocalcinosis[12-14]. Our results are consistent with previous studies that show therapy with rapamycin protected by nanoparticles can significantly reduce kidney damage[11].

Example 8

Cytotoxicity

We evaluated drug cytotoxicity on a panel of human CRC cells. HEK293 cells were included because of their known mTOR signaling activity[15]. The dose-response curves for cell viability are shown, FIG. 4C-H. The in vitro cytotoxicity studies in CRC cells showed less toxicity (higher $IC_{50}$) upon exposure to LTT*-labeled rapamycin micelles compared to free rapamycin, FIG. 4. The $IC_{50}$ values show that LTT*-labeled and plain rapamycin micelles can deliver drug in higher concentrations to each group of cells than free rapamycin (R). In addition, polymer conjugates, LTT*-labeled and unlabeled pegylated octadecyl lithocholate without encapsulated rapamycin, did not show any cytotoxicity up to 10 mg/mL.

These results can be explained by a prolonged drug release from the micelles, variations in basal activation of cancer cell signaling, differences in cell sensitivity to the drug, and unexplored drug effects[16]. Other targeting ligands have been developed to improve efficiency of drug delivery to CRC cells in vitro that have not been demonstrated in vivo. A Fab' antibody fragment has been used to coat the surface of liposomes to increase intracellular uptake in EGFR overexpressing cells[17]. A fibronectin-mimetic peptide (PR-b) has been used to label pH sensitive liposomes for internalization in $a_5\beta_1$ expressing cells[18].

Example 9

Immunohistochemistry of Adenoma Regression

Figure 5:
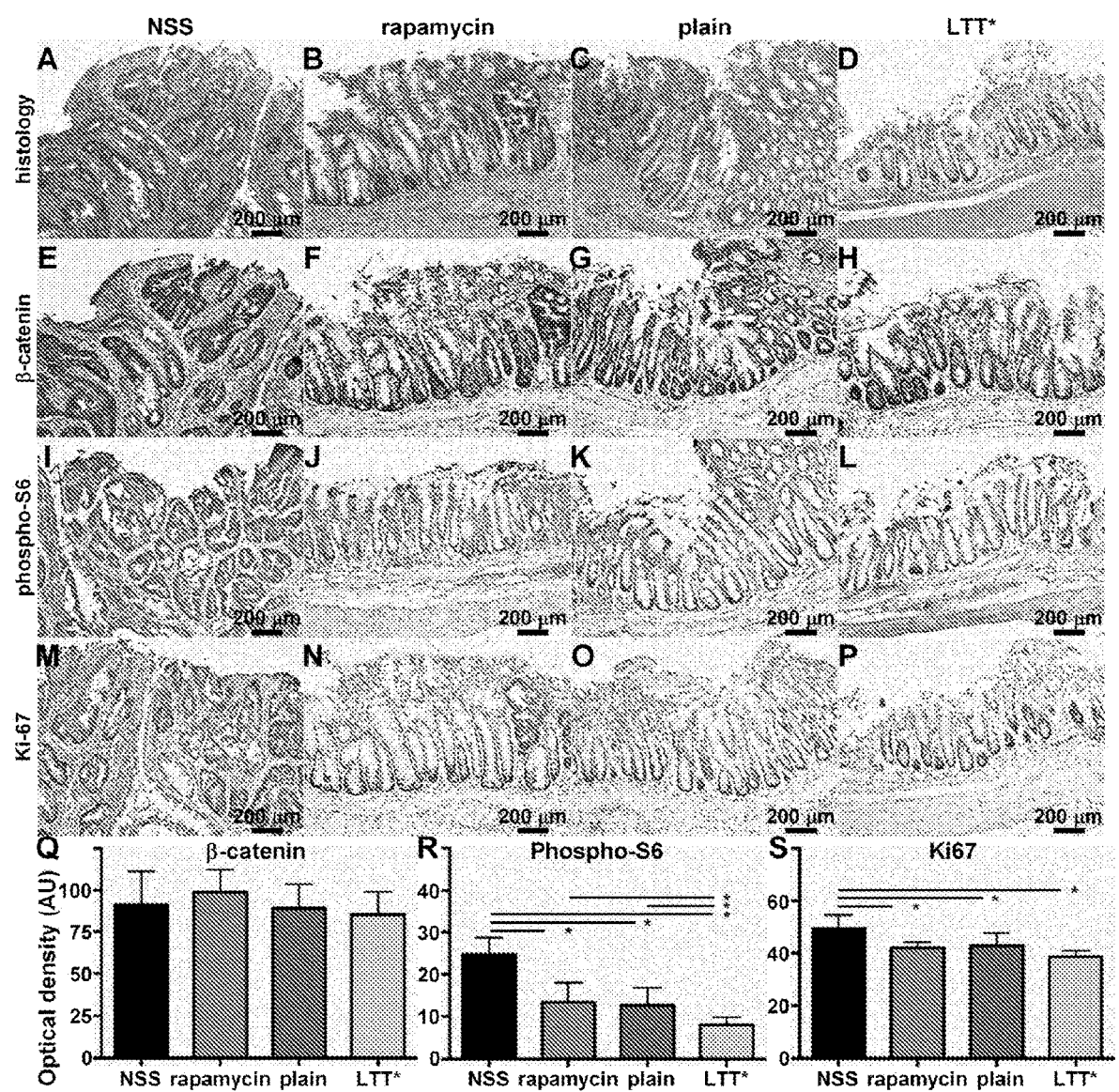
FIG. 5 relates to immunohistochemistry of regressed adenomas. A-D) Representative histology (H&E) of regressed adenomas treated with NSS, free rapamycin, plain rapamycin micelles, and LTT*-labeled rapamycin micelles is shown. E-H) No significant difference was found in ß-catenin staining among the 4 treatment groups, P=0.18 by ANOVA. I-L) Adenomas treated with LTT*-labeled rapamycin micelles showed greater reduction in phospho-S6 staining than free rapamycin, plain rapamycin micelles and NSS, *P<0.05 by ANOVA. M-P) Rapamycin-treated adenomas showed a significant reduction in Ki67 staining compared to NSS, *P<0.05 by ANOVA. Image analysis of integrated optical density shows differences in antibody staining intensity for Q) ß-catenin, R) phospho-S6, and S) Ki67 after 5 weeks of treatment with different rapamycin formulations, *P<0.05 by ANOVA.

Adenomas in the untreated mice (NSS) were found in greater number and with larger tumor volumes on histology (H&E), FIG. 5A. Adenomas in the rapamycin treatment groups showed nearly complete regression after completion of therapy, FIG. 5B-D. The rapamycin treated adenomas showed more regenerative changes, active colitis, submucosal and mucosal scarring, and smaller tumor volumes. Many lesions treated with the LTT*-labeled rapamycin micelles appeared histologically normal, FIG. 5D. On immunohistochemistry, there was no difference in ß-catenin staining between NSS and the rapamycin-treated adenomas, FIG. 5E-H. Expression of phospho-S6 was significantly reduced in all groups of rapamycin treated adenomas compared to NSS, *P<0.05 by ANOVA, FIG. 5I-L. Adenomas treated with LTT*-labeled rapamycin micelles showed a greater reduction in phospho-S6 staining than either plain rapamycin micelles or free rapamycin, *P<0.05 by ANOVA, FIG. 5R, suggesting that greater inhibition of mTOR signaling had occurred. Unremarkable differences in ß-catenin expression suggested that this inhibitory effect occurs downstream of ß-catenin accumulation. This result is consistent with that found in the study by Fujishita et al.[19], whereas the study of Koehl et al.[20] revealed no difference in accumulation of ß-catenin in rapamycin-treated adenomas and normal intestinal epithelium. The rapamycin-treated adenomas showed a significant reduction in Ki67 staining compared to NSS, *P<0.05 by ANOVA, corresponding to decreased tumor cell proliferation, FIG. 5M-P. The optical densities for antibody staining on immunohistochemistry were quantified, FIG. 5Q-S.

DISCUSSION OF RESULTS

In summary, CPC; Apc mice that spontaneously develop colonic adenomas were treated with free rapamycin, plain rapamycin micelles, and peptide-labeled rapamycin micelles via intraperitoneal injection for 35 days. Endoscopy was performed to monitor adenoma regression in vivo. We observed complete adenoma regression at the end of therapy. The mean regression rate for peptide-labeled rapamycin micelles was significantly greater than that for plain rapamycin micelles, P<0.01. On immunohistochemistry, we observed a significant reduction in phospho-S6 but not ß-catenin expression and reduced tumor cell proliferation, suggesting greater inhibition of downstream mTOR signaling. We observed significantly reduced renal toxicity for peptide-labeled rapamycin micelles compared to that of free drug, and no other toxicities were found on chemistries. Together, this unique targeted micelle represents a therapeutic for colorectal neoplasia with comparable therapeutic efficacy to rapamycin free drug and significantly less systemic toxicity.

The results of this study support the use of targeted micelles to encapsulate and deliver hydrophobic anticancer drugs for adjuvant treatment of CRC with reduced systemic toxicity. In addition to rapamycin and other mTOR inhibitors, this methodology may be generalized to encapsulation of other powerful lipophilic drugs, such as doxorubicin, paclitaxel, cyclosporin A, geldanamycin, dipyridamole, and camptothecin, whose widespread clinical use is currently limited by either poor solubility or high toxicity.

While the present invention has been described in terms of specific embodiments, it is understood that variations and modifications will occur to those skilled in the art. Accordingly, only such limitations as appear in the claims should be placed on the invention.

All documents cited in this application are hereby incorporated by reference in their entirety, with particular attention to the disclosure for which they are referred.

CITED DOCUMENTS

[1] J. Tol, C. J. Punt, Monoclonal antibodies in the treatment of metastatic colorectal cancer: a review, Clin. Ther. 32 (2010) 437-453.

[2] A. J. Weickhardt, T. J. Price, G. Chong, V. Gebski, N. Pavlakis, T. G. Johns, A. Azad, E. Skrinos, K. Fluck, A. Dobrovic, Dual targeting of the epidermal growth factor receptor using the combination of cetuximab and erlotinib: preclinical evaluation and results of the phase II DUX study in chemotherapy-refractory, advanced colorectal cancer, J. Clin. Oncol. 30 (2012) 1505-1512.

[3] K. Kim, S. Kwon, J. H. Park, H. Chung, S. Y. Jeong, I. C. Kwon, I.-S. Kim, Physicochemical characterizations of self-assembled nanoparticles of glycol chitosan-deoxycholic acid conjugates, Biomacromolecules 6 (2005) 1154-1158.

[4] S. Kwon, J. H. Park, H. Chung, I. C. Kwon, S. Y. Jeong, I.-S. Kim, Physicochemical characteristics of self-assembled nanoparticles based on glycol chitosan bearing 5Bcholanic acid, Langmuir 19 (2003) 10188-10193.

[5] H. Zhou, W. Yu, X. Guo, X. Liu, N. Li, Y. Zhang, X. Ma, Synthesis and characterization of amphiphilic glycidol-chitosan-deoxycholic acid nanoparticles as a drug carrier for doxorubicin, Biomacromolecules 11 (2010) 3480-3486.

[6] G. B. Fields, R. L. Noble, Solid phase peptide synthesis utilizing 9-fluorenylmethoxycarbonyl amino acids, Int. J. Pept. Protein Res. 35 (1990) 161-214.

[7] H. H. Hensley, C. E. Merkel, W.-C. L. Chang, K. Devarajan, H. S. Cooper, M. L. Clapper, Endoscopic imaging and size estimation of colorectal adenomas in the multiple intestinal neoplasia mouse, Gastrointest. Endosc. 69 (2009) 742-749.

[8] Y.-L. Yao, J. Shao, C. Zhang, J.-H. Wu, Q.-H. Zhang, J.-J. Wang, W. Zhu, Proliferation of colorectal cancer is promoted by two signaling transduction expression patterns: ErbB2/ErbB3/AKT and MET/ErbB3/MAPK, PLoS One 8 (2013) e78086.

[9] X. D. Guo, L. J. Zhang, Y. Chen, Y. Qian, Core/shell pH-sensitive micelles self-assembled from cholesterol conjugated oligopeptides for anticancer drug delivery, AIChE J. 56 (2010) 1922-1931.

[10] M. Wang, M. Thanou, Targeting nanoparticles to cancer, Pharmacol. Res. 62 (2010) 90-99.

[11] M. Shah, M. C. Edman, S. R. Janga, P. Shi, J. Dhandhukia, S. Liu, S. G. Louie, K. Rodgers, J. A. MacKay, S. F. Hamm-Alvarez, A rapamycin-binding protein polymer nanoparticle shows potent therapeutic activity in suppressing autoimmune dacryoadenitis in a mouse model of Sjogren's syndrome, J. Control. Release 171 (2013) 269-279.

[12] D. Choudhury, Z. Ahmed, Drug-associated renal dysfunction and injury, Nat. Clin. Pract. Nephrol. 2 (2006) 80-91.

[13] R. John, A. Herzenberg, Renal toxicity of therapeutic drugs, J. Clin. Pathol. 62 (2009) 505-515.

[14] A. H. Loh, A. H. Cohen, Drug-induced kidney disease-pathology and current concepts, Ann. Acad. Med. Singap. 38 (2009) 240-250.

[15] Y. Fang, M. Vilella-Bach, R. Bachmann, A. Flanigan, J. Chen, Phosphatidic acid mediated mitogenic activation of mTOR signaling, Science 294 (2001) 1942-1945.

[16] J. R. Hasenstein, H.-C. Shin, K. Kasmerchak, D. Buehler, G. S. Kwon, K. R. Kozak, Antitumor activity of Triolimus: a novel multidrug-loaded micelle containing paclitaxel, rapamycin, and 17-AAG, Mol. Cancer Ther. 11 (2012) 2233-2242.

[17] C. Mamot, R. Ritschard, W. Kung, J. W. Park, R. Herrmann, C. F. Rochlitz, EGFRtargeted immunoliposomes derived from the monoclonal antibody EMD72000 mediate specific and efficient drug delivery to a variety of colorectal cancer cells, J. Drug Target. 14 (2006) 215-223.

[18] A. Garg, E. Kokkoli, pH-Sensitive PEGylated liposomes functionalized with a fibronectin-mimetic peptide show enhanced intracellular delivery to colon cancer cells, Curr. Pharm. Biotechnol. 12 (2011) 1135-1143.

[19] T. Fujishita, K. Aoki, H. A. Lane, M. Aoki, M. M. Taketo, Inhibition of the mTORC1 pathway suppresses intestinal polyp formation and reduces mortality in Apc716 mice, Proc. Natl. Acad. Sci. 105 (2008) 13544-13549.

[20] G. Koehl, M. Spitzner, J. Ousingsawat, R. Schreiber, E. Geissler, K. Kunzelmann, Rapamycin inhibits oncogenic intestinal ion channels and neoplasia in APCMin/+ mice, Oncogene 29 (2010) 1553-1560.

[21] S. J. Miller, K. A. Heist, Y. Feng, C. J. Galban, A. Rehemtulla, B. D. Ross, E. R. Fearon, T. D. Wang, Multimodal imaging of growth and rapamycin-induced regression of colonic adenomas in apc mutation-dependent mouse, Translational oncology, 5 (2012) 313-320.

We claim:

1. A micelle comprising block co-polymers of the structure A-B-C, wherein hydrophobic component A is a bile acid, hydrophilic component B is a polymer and C is a targeting peptide,
wherein the bile acid is octadecyl lithocholate, and
wherein the peptide is NGTTSSNNQLINENNIQN (SEQ ID NO: 1), EHMYNTPHTYHTTMKNNK (SEQ ID NO: 2), QPIHPNNM (SEQ ID NO: 3), NKLAAALE (SEQ ID NO: 4), KNYKN (SEQ ID NO: 5), TNTHN (SEQ ID NO: 6), KHTNN (SEQ ID NO: 7), SILPYPY (SEQ ID NO: 8), KCCFPAQ (SEQ ID NO: 9), YRAPWPP (SEQ ID NO: 10), QPWPTSI (SEQ ID NO: 11), WPTPPYA (SEQ ID NO: 12), MHAPPFY (SEQ ID NO: 13), VRPTLPM (SEQ ID NO: 14), NFMESLPRLGMH (SEQ ID NO: 15), HYKL (SEQ ID NO: 16), AKPGYLS (SEQ ID NO: 17), LTTHYKL (SEQ ID NO: 18), QRHKPRE (SEQ ID NO: 19), HAHRSWS (SEQ ID NO: 20), YLTMPTP (SEQ ID NO: 21), TYPISFM (SEQ ID NO: 22), KLPGWSG (SEQ ID NO: 23), IQSPHFF (SEQ ID NO: 24), YSIPKSS (SEQ ID NO: 25), SHRNRPRNTQPS (SEQ ID NO: 26), NRHKPREKTFTD (SEQ ID NO: 27), TAVPLKRSSVTI (SEQ ID NO: 28), GHTANRQPWPND (SEQ ID NO: 29), LSLTRTRHRNTR (SEQ ID NO: 30), RHRDTQNHRPTN (SEQ ID NO: 31), ARHRPKLPYTHT (SEQ ID NO: 32), KRPRTRNKDERR (SEQ ID NO: 33), SPMPQLSTLLTR (SEQ ID NO: 34), NHVHRMHATPAY (SEQ ID NO: 35), RTSPSSR (SEQ ID NO: 36), HLQLQRL (SEQ ID NO: 37), IQTNPTM (SEQ ID NO: 38), RSLTQQT (SEQ ID NO: 39), SLQHLRS (SEQ ID NO: 40), IQLKINS (SEQ ID NO: 41), ITIRQHI (SEQ ID NO: 42), RRSNSQL (SEQ ID NO: 43), LNRIRRR (SEQ ID NO: 44), NNMKKIT (SEQ ID NO: 45), LQSLISK (SEQ ID NO: 46), IHTRRRK (SEQ ID NO: 47), RPNKPRI (SEQ ID NO: 48), RHRRSPI (SEQ ID NO: 49), ITLSITQ (SEQ ID NO: 50), KTQLMII (SEQ ID NO: 51), RPRQLQR (SEQ ID NO: 52), TRRHTII (SEQ ID NO: 53), RIIHKNM (SEQ ID NO: 54), LLTISPK (SEQ ID NO: 55), LLPMHMN (SEQ ID NO: 56), TSPMLSI (SEQ ID NO: 57), LRNNIRH (SEQ ID NO: 58), KSPNPRF (SEQ ID NO: 59), RHPFPRF (SEQ ID NO: 60), RHPWPNR (SEQ ID NO: 61), RHPYPQR (SEQ ID NO: 62) or RKPFPRH (SEQ ID NO: 63).

2. The micelle of claim 1 wherein the polymer is methoxy poly(ethylene) glycol (PEG) amine or thiol PEG amine.

3. The micelle of claim 2 wherein the polymer is thiol PEG amine.

4. The micelle of claim 1 wherein the targeting peptide binds to a colorectal cancer cell.

5. The micelle of claim 1 wherein the targeting peptide is LTTHYKL (SEQ ID NO: 18).

6. The micelle of claim 1 or 5 further comprising a drug.

7. The micelle of claim 6 wherein the drug is rapamycin, doxorubicin, paclitaxel, cyclosporin A, geldanamycin, dipyridamole or camptothecin.

8. The micelle of claim 7 wherein the drug is rapamycin.

9. A dosage form comprising the micelle of claim 8.

10. A method of treating colorectal cancer in a patient, comprising administering to the patient a dosage form of claim 9.

11. A dosage form comprising the micelle of claim 1.

* * * * *